United States Patent [19]

Suzuki et al.

[11] Patent Number: 4,924,852
[45] Date of Patent: May 15, 1990

[54] ENDOSCOPE

[75] Inventors: Akira Suzuki; Yoshikatsu Nagayama; Michio Sato; Koji Yamaya; Koji Kanbara; Akira Hasegawa, all of Tokyo; Masaaki Hayashi, Iruma; Hideo Adachi, Tokyo; Takeaki Nakamura, Tokyo, all of Japan

[73] Assignee: Olympus Optical Co., Ltd., Tokyo, Japan

[21] Appl. No.: 241,373

[22] Filed: Sep. 7, 1988

[30] Foreign Application Priority Data

| Sep. 11, 1987 [JP] | Japan | 62-139196[U] |
| Oct. 16, 1987 [JP] | Japan | 62-261199 |
| Jan. 11, 1988 [JP] | Japan | 63-1920[U] |
| Jan. 11, 1988 [JP] | Japan | 63-3599 |
| Feb. 3, 1988 [JP] | Japan | 63-12559[U] |

[51] Int. Cl.$^5$ ............................................. A61B 1/00
[52] U.S. Cl. ..................................................... 128/4
[58] Field of Search ............... 128/4; 310/311 R, 313, 310/328, 330, 333, 369

[56] References Cited

U.S. PATENT DOCUMENTS

| 4,562,373 | 12/1985 | Tokusima et al. | 310/328 |
| 4,689,516 | 8/1987 | Yokoyama et al. | 310/328 X |
| 4,723,085 | 2/1988 | Mukohjima et al. | 310/328 |
| 4,743,791 | 5/1988 | Kawai | 310/328 X |

FOREIGN PATENT DOCUMENTS 106126 5/1986 Japan ............................ 128/662.06

Primary Examiner—Francis Jaworski
Attorney, Agent, or Firm—Frishauf, Holtz, Goodman & Woodward

[57] ABSTRACT

An endoscope, which has an insertion section with a moving part, comprises a stator for generating a surface wave as a combination of a transverse wave and a longitudinal wave; a rotor rotatably disposed facing the stator; an urging mechanism for bringing the rotor intimately into contact with the stator; a coupling member coupled to the rotor and adapted to cause the moving part of the endoscope to operate as the rotor rotates; and a disengaging mechanism for releasing the stator and the rotor from the intimate contact with each other.

18 Claims, 32 Drawing Sheets

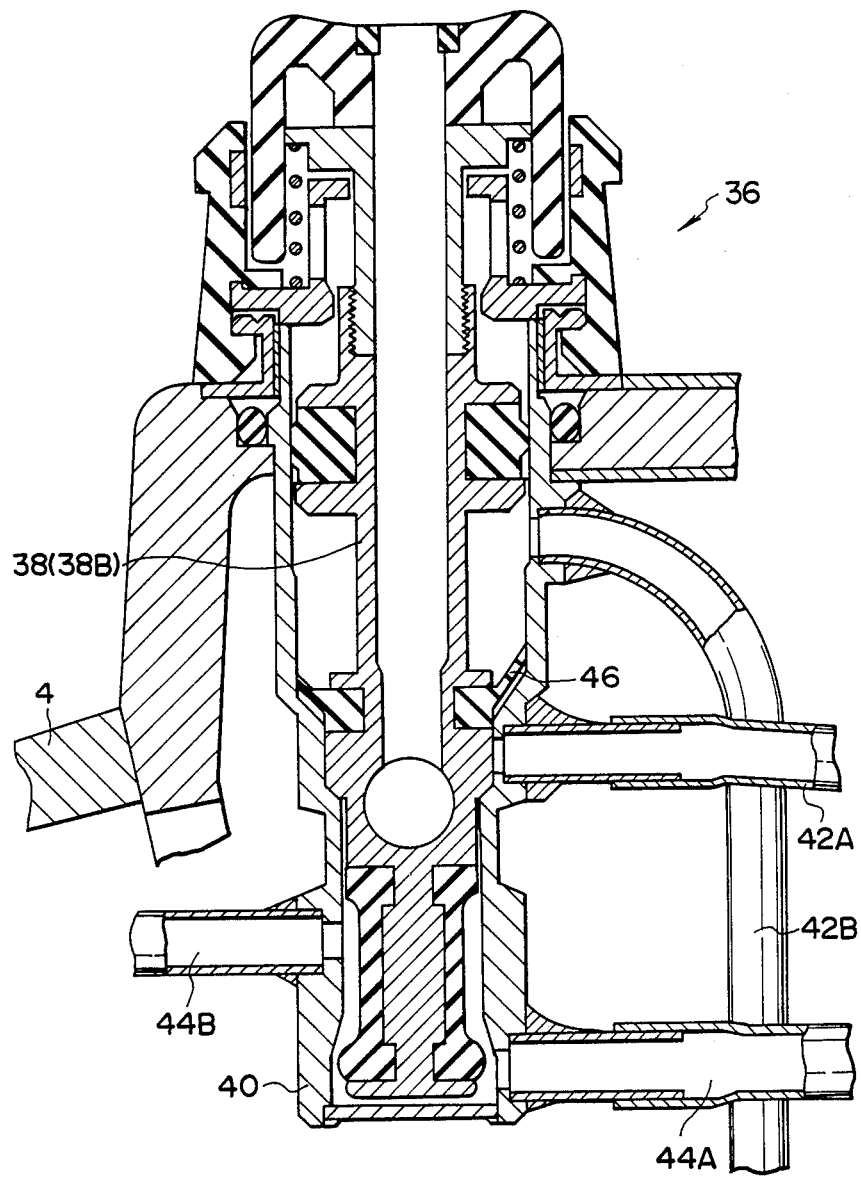
F I G. 6

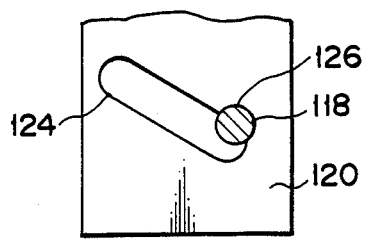
F I G. 12
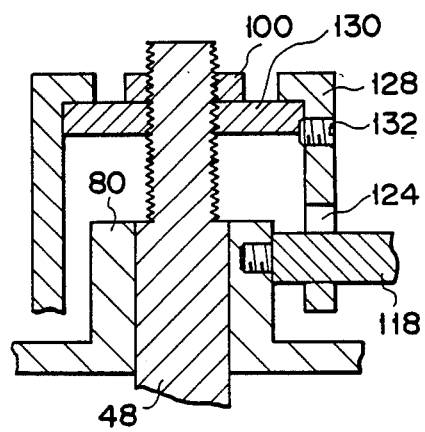
F I G. 13

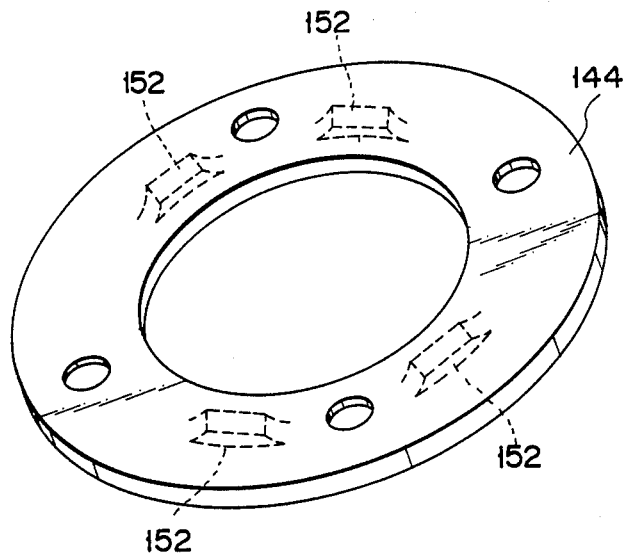
F I G. 15
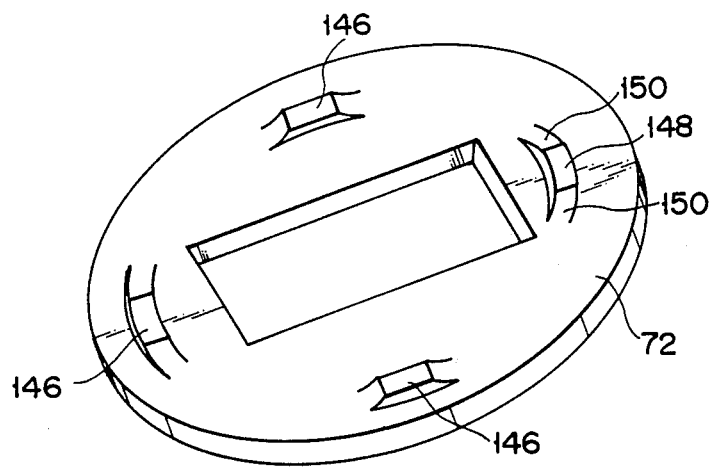
F I G. 16

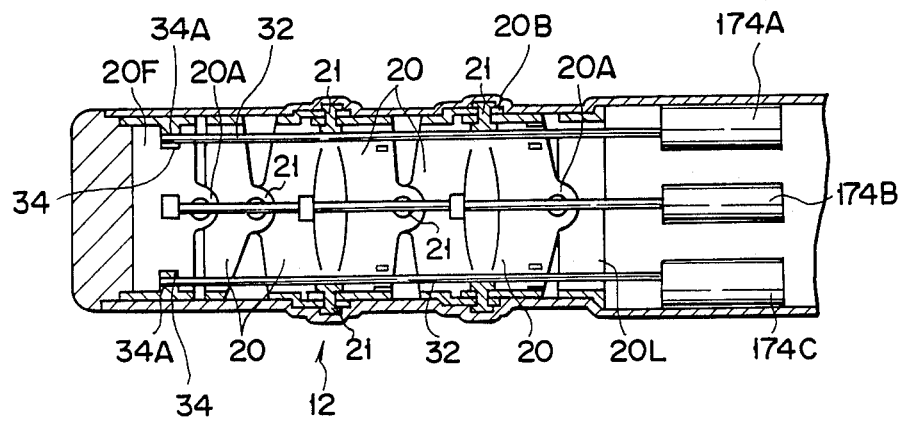
F I G. 22
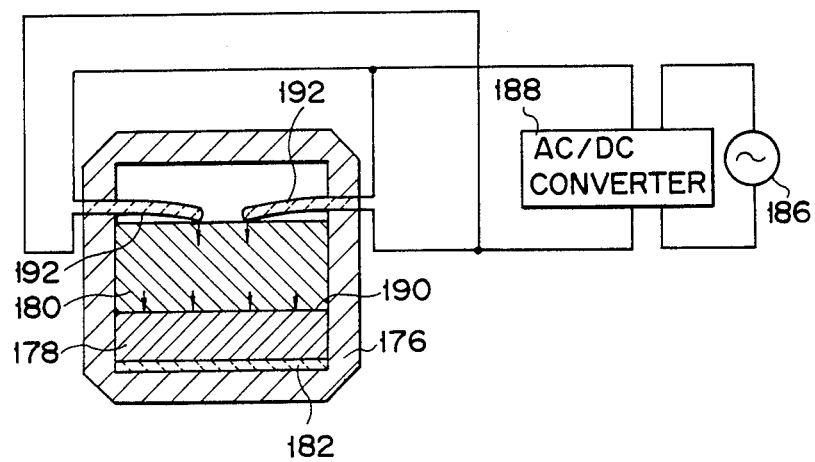
F I G. 23

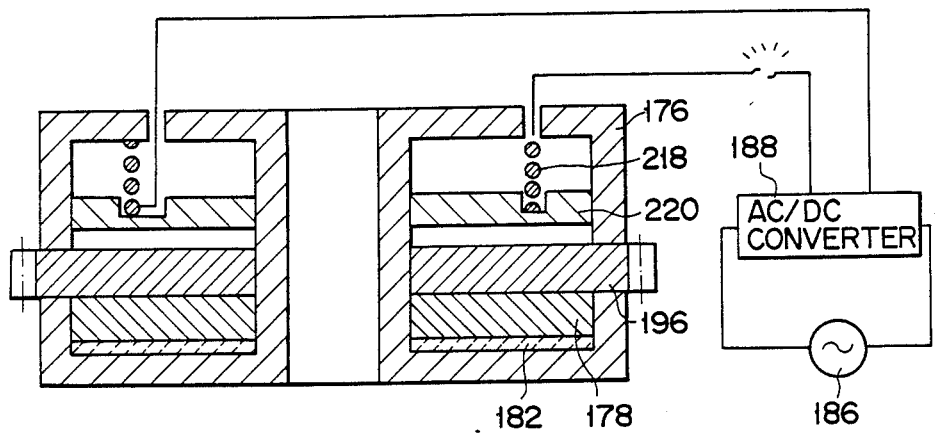
F I G. 32

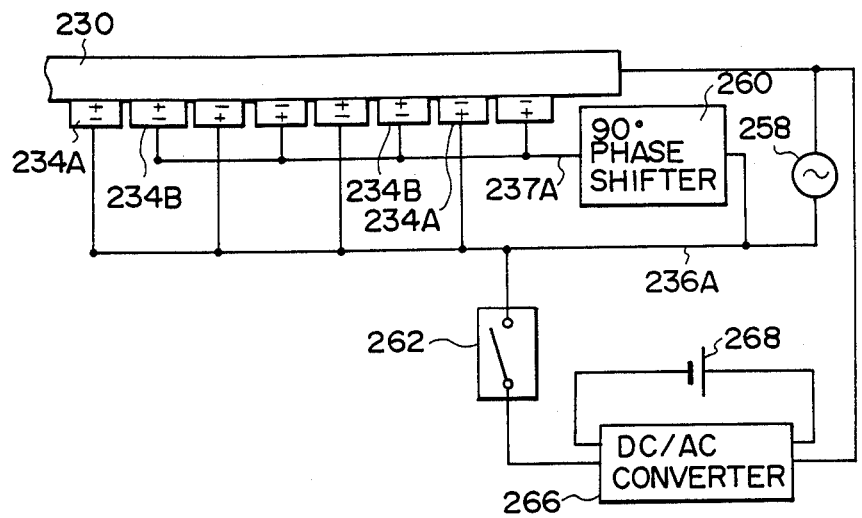
F I G. 38
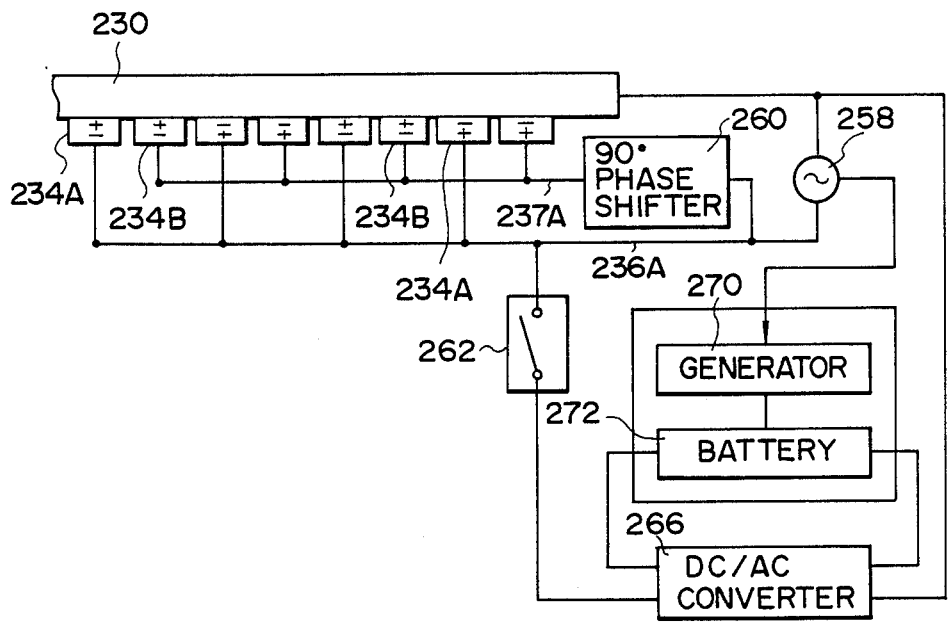
F I G. 39

ENDOSCOPE

BACKGROUND OF THE INVENTION

A. Field of the Invention

The present invention relates to an endoscope in which a moving part of its insertion section is driven by means of a motor which utilizes the vibration of a vibrator for rotation.

B. Description of the Related Art

Disclosed in Japanese Patent Disclosure No. 61-106126 is an endoscope in which a moving part, e.g., a bending portion, of its insertion section is bent by means of a motor which rotates by utilizing the vibration of a vibrator. The vibrating-type motor of this endoscope comprises a rotor, a stator, and an urging member for bringing the stator into intimate contact with the rotor. The rotor is connected to one end of an operating wire, the other end of which is coupled to the bending portion of the insertion section. As a vibration is produced between the rotor and the stator, the rotor is rotated by the agency of progressive waves, whereby the bending portion is bent by means of the operating wire.

In the conventional endoscope using the vibrating-type motor, when the motor is energized, the rotor, and hence, the bending portion connected thereto, can be freed by producing standing waves between the rotor and the stator. In case of power failure, however, the rotor and the stator will be pressed against the urging member, and fixed by means of frictional force between themselves. As a result, the bending portion will be locked.

If a control circuit for driving the vibrating-type motor goes wrong, moreover, the bending portion of the insertion section will not be able to be freed.

SUMMARY OF THE INVENTION

The object of the present invention is to provide an endoscope having a mechanism which can press a rotor and a stator of a vibrating-type motor against each other or release them from the engagement, thereby freeing a bending portion connected to the rotor, so that the safety of the endoscope is improved.

The above object of the present invention is achieved by an endoscope constructed as follows.

The endoscope comprises an insertion section with a moving part, a stator for generating a surface wave as a combination of a transverse wave and a longitudinal wave, a rotor rotatably disposed facing the stator, an urging member for bringing the rotor into intimate contact with the stator, a coupling member coupled to the rotor and adapted to cause the moving part of the endoscope to operate as the rotor rotates, and a disengaging mechanism for releasing the stator and the rotor from the intimate contact with each other.

As described above, the endoscope according to the present invention is provided with the mechanism for engagement or disengagement between the rotor and the stator of a vibrating-type motor. In this arrangement, the rotor and the stator can be released, as required, from pressure contact with each other, thereby freeing a bending portion of the insertion section connected to the rotor.

Thus, the safety of the endoscope can be ensured even in case of a power failure or trouble.

BRIEF DESCRIPTION OF THE DRAWINGS

FIG. 6 is a longitudinal sectional view showing a modification of the selector valve;

FIG. 12 is a sectional view taken along line H—H of FIG. 11;

FIG. 13 is a sectional view showing a modification of a cam body;

FIGS. 15 and 16 are perspective views of components shown in FIGS. 14 and 17, respectively;

FIG. 22 is a longitudinal sectional view of an insertion section shown in FIG. 21;

FIGS. 23 and 24 are sectional views of a wire drive unit according to a first modification of the second embodiment;

FIGS. 31 and 32 are sectional views of a wire drive unit according to a seventh modification of the second embodiment;

FIG. 38 is a block diagram of a control circuit according to a first modification of the third embodiment;

FIG. 39 is a block diagram of a control circuit according to a second modification of the third embodiment;

DETAILED DESCRIPTION OF THE PREFERRED EMBODIMENTS

Figure 1:
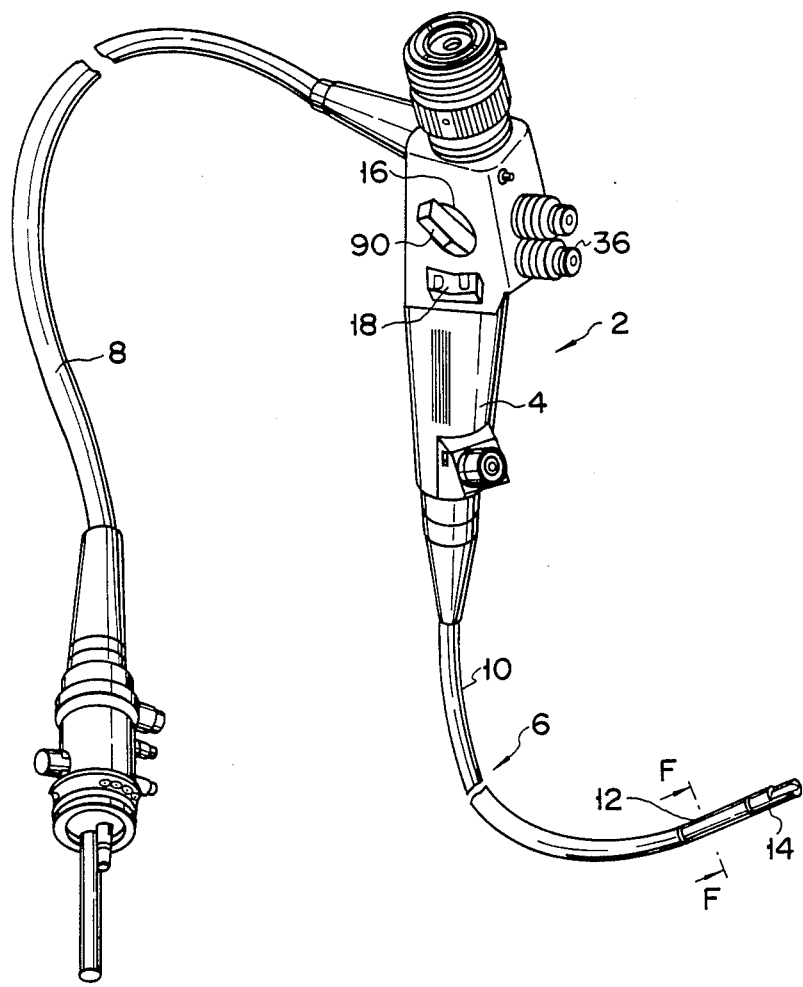
FIG. 1 is a perspective view of an endoscope according to a first embodiment of the present invention.

FIGS. 1 to 10 show a first embodiment of the present invention. Endoscope 2 shown in FIG. 2 comprises control section 4, insertion section 6, and universal cord 8. In insertion section 6, bending tube 12 and distal end structure 14 are coupled in succession to the distal end of flexible tube 10. Control section 4 is provided with control switch 18 and bending control unit 16, used to remotely bend tube 12 of section 6.

Figure 3:
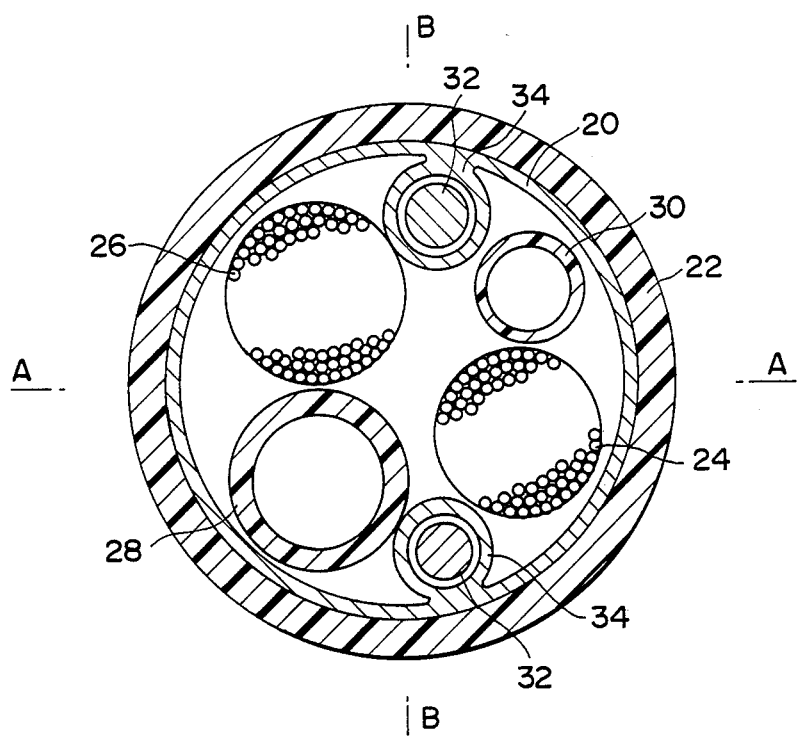
FIG. 3 is a sectional view taken along line F—F of FIG. 1.

FIG. 3 shows the construction of bending tube 12 of insertion section 6. Tube 12 includes a plurality of links 20 and elastic member 22 covering the same. Links 20, which are arranged in the longitudinal direction of insertion section 6, are rockably coupled to each other by means of pivot pins (not shown). Bending tube 12 contains illumination light transmission member 24, image transmission member 26, instrument channel 28, fluid channel 30, operating wires 32 used to bend bending tube 12, and a plurality of guide rings 34 for guiding wires 32. Each ring 34 is fixed to the inner wall surface of its corresponding link 20 by brazing or by means of a bonding agent. The fixing position of each ring 34 is slightly deviated from a plane (line B—B of FIG. 3) which passes through the center of link 20 at right angles to the axis (line A—A of FIG. 3) of each pivot pin. The sum of the respective rigidities of the elements contained in the region on the right of line B—B of FIG. 3 is different from that in the region on the left of the line. A clearance is provided between the pivot pin and a pivot pin hole (not shown) formed in each link 20.

Figure 2:
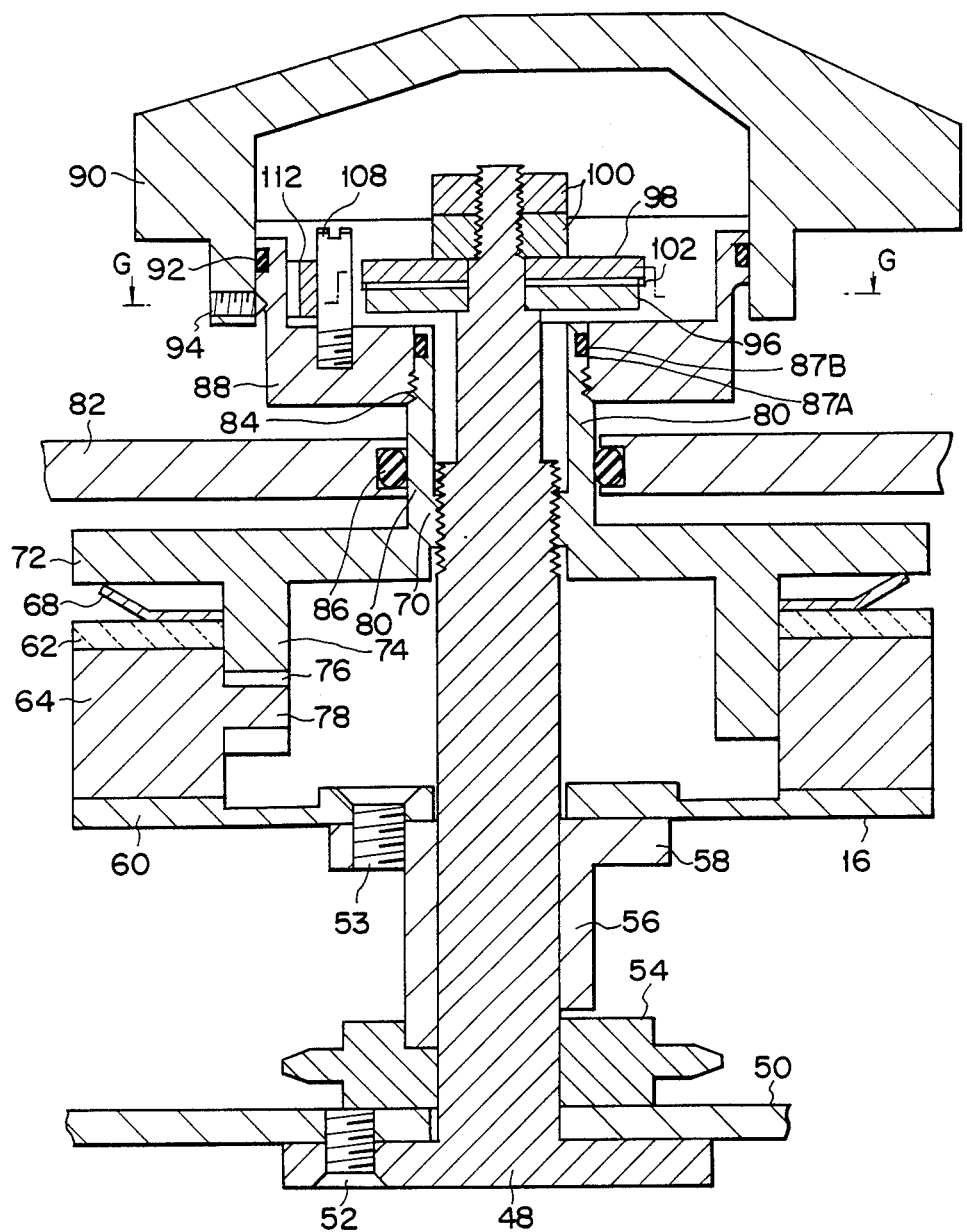
FIG. 2 is a longitudinal sectional view showing a bending control unit of the endoscope shown in FIG. 1.
Figure 5:
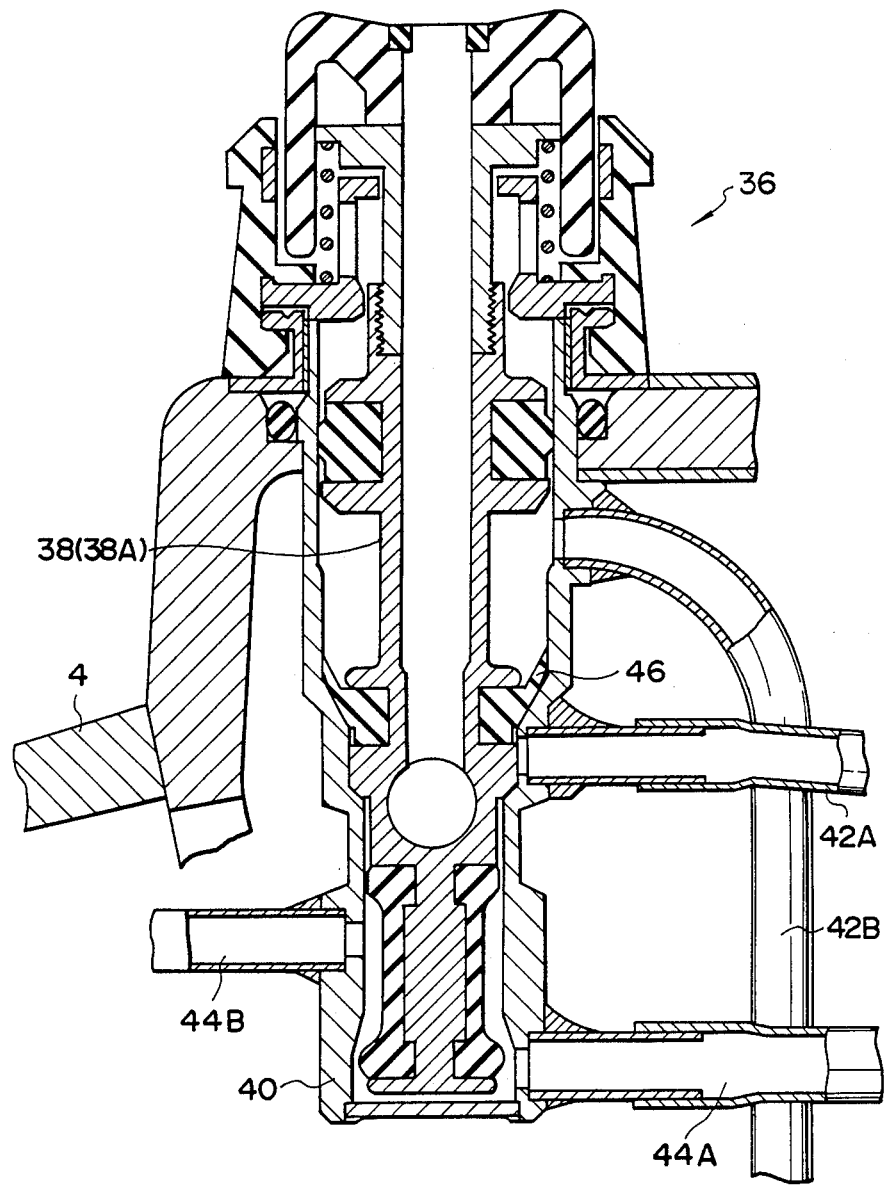
FIG. 5 is a longitudinal sectional view of a selector valve according to the first embodiment.
Figures 7, 8:
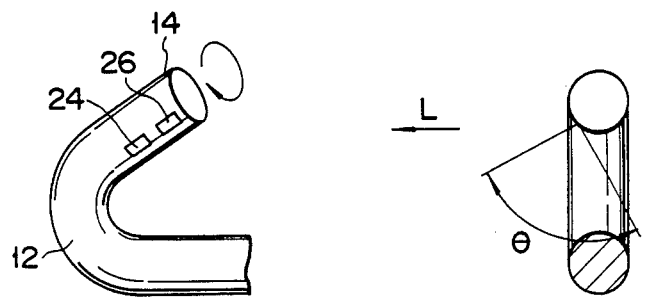
FIGS. 7 and 8 are a side view and a front view, respectively, of an insertion section according to the first embodiment.

As shown in FIG. 2, control section 2 is provided with selector valve 36 (FIG. 5) for regulating the amounts of water and air ejected from a nozzle at distal end structure 14. As shown in FIG. 5, valve 36 includes cylinder 40 and piston 38 fitted therein. Cylinder 40 is connected with upstream-side air duct 42A, upstream-side water duct 44A, downstream-side air duct 42B, and downstream-side water duct 44B, individually. Either of two types of buttons 38A and 38B is used as piston 38 attached to cylinder 40. When using first piston 38A, the operation can be shifted between three modes, i.e., air feed, water feed, and stop, by depressing piston 38B. FIG. 5 shows a water feed mode of selector valve 36 established when first piston 38A is attached to cylinder 40, while FIG. 6 shows a water/air feed mode established when second piston 38B is attached. First and second pistons 38A and 38B are different in the position of valve 46. In FIG. 5, the duct is fully closed by valve 46. In FIG. 6, on the other hand, the duct is not fully closed by valve 46, so that air is also fed during water feed. Thus, an operator can use the endoscope either as one capable of water feed operation or as another capable of air/water feed operation, by selecting detachable piston 38 (38A or 38B).

The following is a description of bending control unit 16. Control unit 16 shown in FIG. 1 has stationary shaft 48, whose proximal end portion is fixed to frame member 50 of control section 4 by means of fixing screw 52. Sprocket 54 is rotatably mounted on shaft 48, and chain (not shown), which is in engagement with sprocket 54, is connected to operating wires 32. Sleeve 56, which is fitted on stationary shaft 48, is coupled at one end to sprocket 54 so as to be nonrotatable. Disk-shaped rotor 60 is fixed to flange 58 which is formed at the other end of sleeve 56. Cylindrical stator 66, including vibrator 62 and vibration transmitter 64, is mounted on the top surface of rotor 60. Leaf spring 68 and pressure member 72 are mounted in layers on the top surface of vibrator 62. Member 72 has left-handed screw portion 70, which is in left-handed engagement with stationary shaft 48, and cylinder portion 74. The outside diameter of portion 74 is a little smaller than the inside diameters of leaf spring 68 and stator 66. Cylinder portion 74 is fitted in stator 66, and notch 76 is formed in the end edge of cylinder portion 74, along part of the circumference thereof. Projection 78 is formed on the inside of cylindrical vibration transmitter 64. It is adapted to engage notch 76 of cylinder portion 74 to make transmitter 64 nonrotatable. By this engagement, vibration transmitter 64 and pressure member 72 are prevented from relative rotation, although transmitter 64 is allowed to move vertically. Second cylinder portion 80, which is formed on the opposite side of member 72 to cylinder portion 74, projects through casing 82 of control section 4 to the outside. Screw portion 84 is formed on the outer periphery of the outer end portion of second cylinder portion 80. Also, O-ring 86 is interposed between cylinder portion 80 and casing 82, whereby the inside of casing 82 is kept water-tight. Screw portion 84 is threadedly fitted in pusher 88 which operates in one with pressure member 72. Bag-shaped control knob 90, which covers the top of pusher 88, is fixed to the outer peripheral surface of pusher 88 by means of a plurality of setscrews 94, with O-ring 92 between knob 90 and pusher 88. Pusher 88 and second cylinder portion 80 of pressure member 72 are pressed in a water-tight manner against each other, with the aid of O-ring 87B in O-ring groove 87A on cylinder portion 80.

Figure 4:
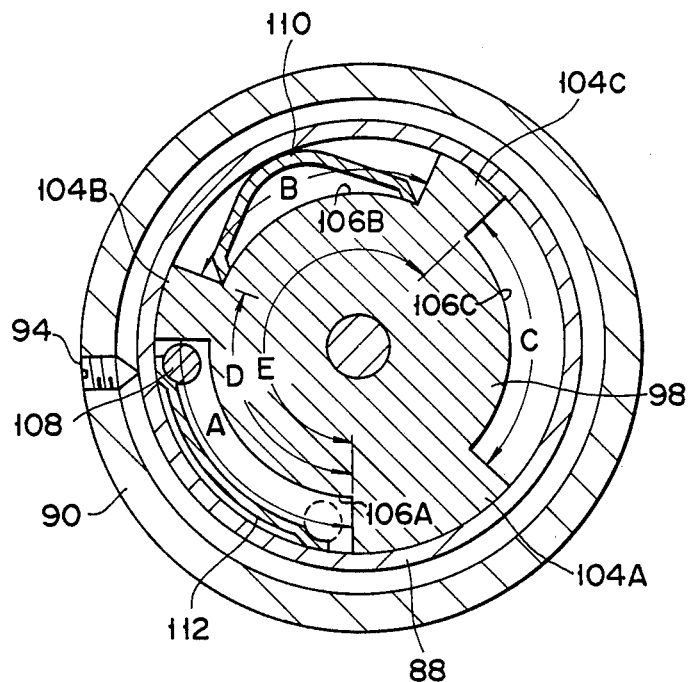
FIG. 4 is a sectional view taken along line G—G of FIG. 2.

First and second toothed plates 96 and 98, which are secured to stationary shaft 48 for nonrotation and rotation, respectively, are mounted on the top surface of pusher 88. Plates 96 and 98 are fixed by means of nuts 100 which are screwed on the extreme end of stationary shaft 48. A number of mating teeth 102 are formed on the respective joint surfaces of toothed plates 96 and 98, at regular pitches along the circumferences of the toothed plates. As shown in FIG. 4, three tongues 104A, 104B and 104C protrude radially outward from second toothed plate 98. Thus, first, second, and third regulation recesses 106A, 106B and 106C are defined along the circumference of plate 98 by tongues 104A, 104B and 104C. Angles A, B and C for recesses 106A, 106B and 106C, with respect to the center of rotation of plate 98, are equal to one another. As for angles D and E indicative of the relative positions of recesses 106A, 106B and 106C, D equals an integral multiple of the pitch of teeth 102 plus ⅓ pitch, and E equals an integral multiple of the pitch of teeth 102 plus ⅔ pitch. Rocking regulation pin 108, which protrudes from the top of pusher 88, is fitted in one of these recesses, e.g., first regulation recess 106A of angle A. Thus, pusher 88 is allowed to rock within the range of angle A of recess 106A.

In the mechanism described above, the position of rocking regulation pin 108 can be changed with every pitch of teeth 102 by changing the position of second toothed plate 98 relative to first toothed plate 96. In this manner, the depth of screw engagement of pusher 88 can be changed. Thus, the frictional force between stator 66 and rotor 60 can be adjusted by regulating the amount of deformation of leaf spring 68 with every pitch width of teeth 102. By shifting the position of pin 108 into second or third regulation recess 106B or 106C, moreover, the position of pin 108 can be finely varied for a third of each pitch of teeth 102. In other words, the depth of screw engagement of pusher 88 can be adjusted in stages thrice as many as the teeth of first toothed plate 96. Positioning spring 110 and click spring 112 are disposed on the top surface of pusher 88. Spring 110 serves to prevent dislocation between first and second toothed plates 96 and 98. Spring 112 is adapted to resiliently engage rocking regulation pin 108 in the final stage of rocking when pusher 88 rocks within the predetermined range.

In assembling bending control unit 16, first and second toothed plates 96 and 98 are engaged with each other in a manner such that the force of pressure contact between rotor 60 and stator 66 is optimum when rocking regulation pin 108 is moved to one end (indicated by broken line in FIG. 4) of click spring 112.

In normal operation of the endoscope, control knob 90 is situated in its dead end position for left-handed turn. Thereupon, rocking regulation pin 108 is situated in the position indicated by broken line in FIG. 4, pressure-control member 72 is lowered by the action of left-handed portion 70, and rotor 60 and stator 66 are pressed against each other under a proper pressure produced by the resilient force of leaf spring 68. If bending control unit 16 is worked in this state, rotor 60 and stator 66 operate as a vibration-wave motor. As stator 66 rotates, operating wires 32 are pulled to bend bending tube 12 of insertion section 6.

In case of power failure or trouble, or in removing insertion section 6 from the body cavity, section 6 is freed by turning operating knob 90 to its dead end position for right-handed turn. Thereupon, rocking regulation pin 108 is situated in the position indicated by full line in FIG. 4. Accordingly, pressure member 72 is moved to the upper portion of stationary shaft 48 by the action of left-handed portion 70, so that rotor 60 and stator 66 are disengaged from each other. As a result, rotor 60 is allowed to rotate around shaft 48. When bending tube 12 is bent, it brought into a neutral state by the resilience of the contents thereof. When an external force is applied to distal end structure 14, bending tube 12 acts freely, depending on the external force. Therefore, insertion section 6 will never press the body wall by force.

Figures 9, 10:
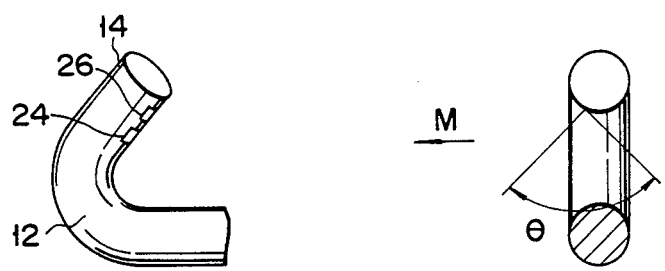
FIGS. 9 and 10 are a side view and a front view respectively, showing a modification of the insertion section.

In the endoscope according to this embodiment, when insertion section 6 is bent, distal end structure 14 is twisted for the clearance between the pivot pin and the pivot pin hole, with respect to the central axis of bending tube 12, since guide rings 34 are deviated from line B—B of FIG. 3. Thus, insertion section 6 can be shifted aside from the center of a field of vision when the bending angle of tube 12 is 90° or more (see FIGS. 7 and 8). The same effect can be also obtained because the sum of the respective rigidities of the elements contained in the region on the right of line B—B of FIG. 3 is different from that in the region on the left of the line. FIGS. 9 and 10 show a state that the insertion section is not twisted.

Figure 11:
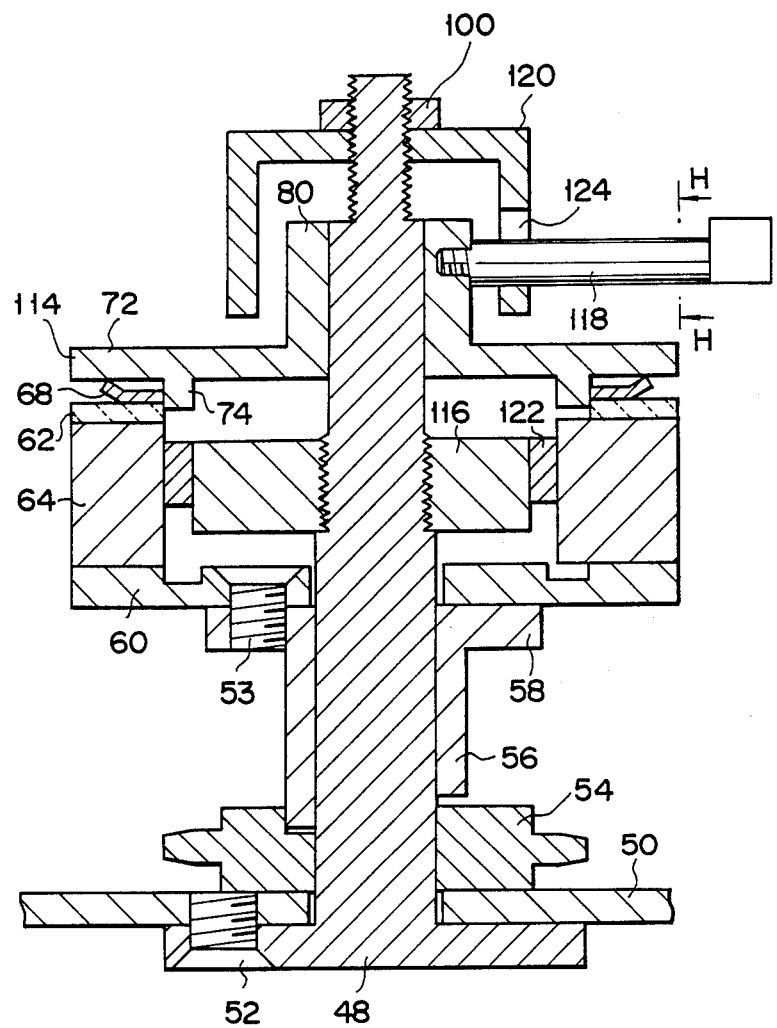
FIG. 11 is a longitudinal sectional view showing a first modification of the bending control unit.
Figure 14:
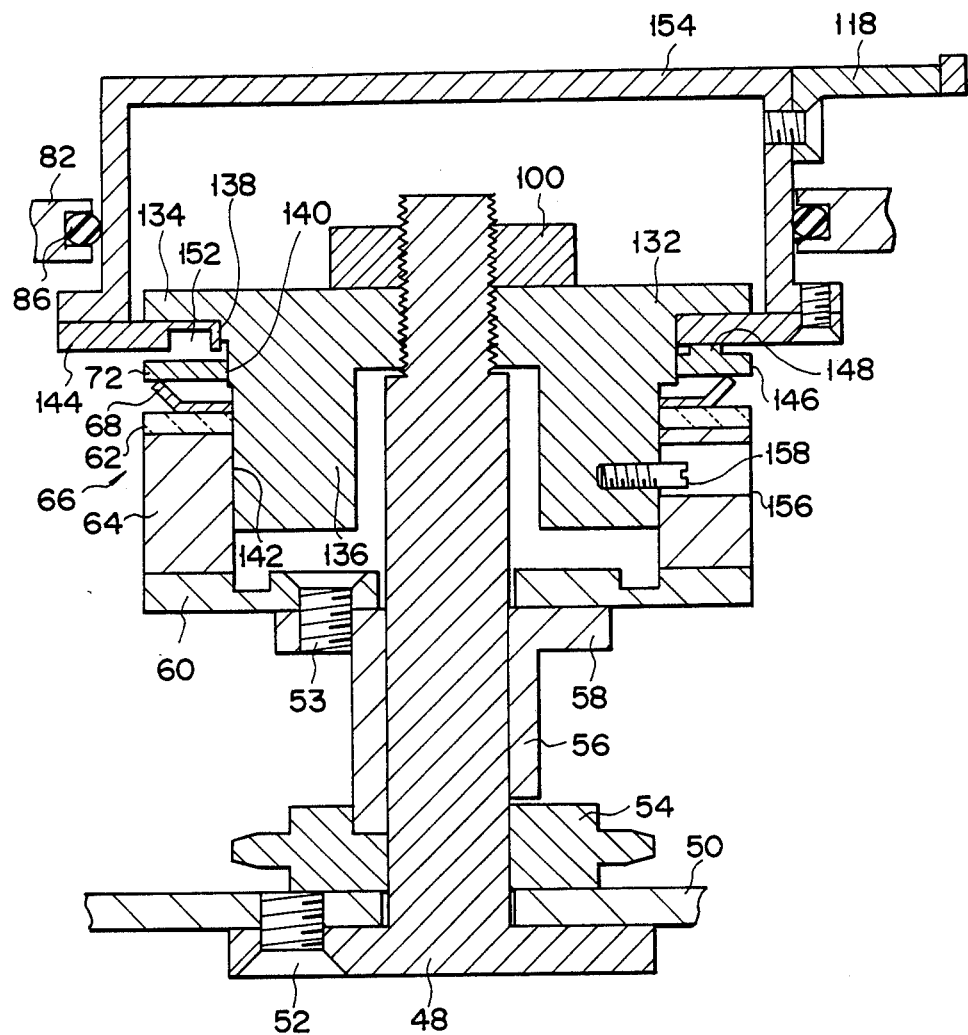
FIGS. 14 and 17 are longitudinal sectional views showing a second modification of the bending control unit.

FIGS. 11 and 12 show a first modification of the first embodiment. This modification is different in the shapes of pressure member 72 and vibration transmitter 64 and in the mechanism of the working portion of control knob 90. More specifically, member 72 is rotatably fitted on stationary shaft 48, and its flange portion 114 causes rotor 60 and stator 66 to be pressed against each other by means of leaf spring 68. Cylinder portion 74 protrudes downward from flange portion 114 so that its outside diameter is equal to the inside diameter of vibrator 62. Thus, stator 66 is kept coaxial with stationary shaft 48. The outer peripheral portion of rotation stopper 116, which is threadedly fitted on shaft 48, has a rectangular section. With the aid of vibration absorber 122, such as rubber, having a predetermined thickness, stopper 116 prevents rotation of vibration transmitter 64 whose inner peripheral surface corresponds to the outer peripheral surface of stopper 116. Control lever 118 is fixed, by screwing, to the outer peripheral surface of cylinder portion 80, which is formed on the top of pressure member 72. Cam slot 124 is formed in the outer periphery of cam body 120 which is nonrotatable with respect to stationary shaft 48. Slot 124 engages control lever 118, thereby restricting the range of rotation of lever 118. Also, slot 124 causes lever 118 to move up and down while it is rotating, thereby vertically moving pressure member 72. Retaining portion 126 is formed at the lower end portion of cam slot 124. Lever 118 and retaining portion 126 constitute a click mechanism.

In assembling bending control unit 16 of this modification, the position of cam body 120 is set so that the force of pressure contact between rotor 60 and stator 66 is best suited for the vibration-wave motor when control lever 118 engages retaining portion 126, and cam body 120 is fixed to stationary shaft 48 by means of nut 100.

In starting the operation of the endoscope, control lever 118 is situated at retaining portion 126. Bending tube 12 can be freed by turning lever 118 to its dead end position for left-handed turn.

FIG. 13 shows a modification of the cam body. In this modification, cam body 120 according to the first embodiment is composed of two parts. More specifically, cam body 128, having cam slot 124, and receiver 130 screwed to stationary shaft 48 are fixed by means of fixing nut 100.

In this modification, moreover, cam body 128 can be fixed at any circumferential position relative to receiver 130, so that control lever 118 can be set in a desired position.

FIGS. 14 to 17 show a second modification of the first embodiment. This modification is different in the shapes of vibration transmitter 64 and pressure member 72 and in the arrangement of the working portion of control knob 90. More specifically, adjuster 132, which is screwed to an end portion of stationary shaft 48, includes flange portion 134 and cylindrical body 136. Having a profile stepped at three points, body 136 includes first circular portion 138, rectangular portion 140 smaller than portion 138, and second circular portion 142 smaller than portion 140, arranged from the side of flange portion 134. Stator 66, leaf spring 68, pressure member 72, grooved member 144, and flange portion 134 are stacked in layers in the order named. As shown in FIG. 16, pressure member 72 has rectangular opening 141 in which rectangular portion 140 of cylindrical body 136 is fitted. Four projections 146 protrude upward from the top surface of pressure member 72. Each projection 146 has flat portion 148 and slope portions 150 on either side thereof. As shown in FIG. 15, grooved member 144 is a disk-shaped structure which has four grooves 152, on the underside thereof, adapted to engage projections 146 of pressure member 72. Grooved member 144, lever support 154, and control lever 118 slidingly rotate in one with first circular portion 138 of cylindrical body 136. Through hole 156 is bored through that portion of vibration transmitter 64 near a neutral plane for vibration thereof. Fixing screw 158 is screwed to cylindrical body 136 through hole 156, so that transmitter 64 is nonrotatable with respect to body 136, but is movable in the axial direction of stationary shaft 48.

In assembling bending control unit 16 of in this second modification, the position of adjuster 132 relative to stationary shaft 48 is set so that the force of pressure contact between rotor 60 and stator 66 is best suited for the vibration motor when grooves 152 of grooved member 144 are not in engagement with projections 146 of pressure member 72 (state shown in FIG. 4), and adjuster 132 is fixed by means of nut 100.

Figure 17:
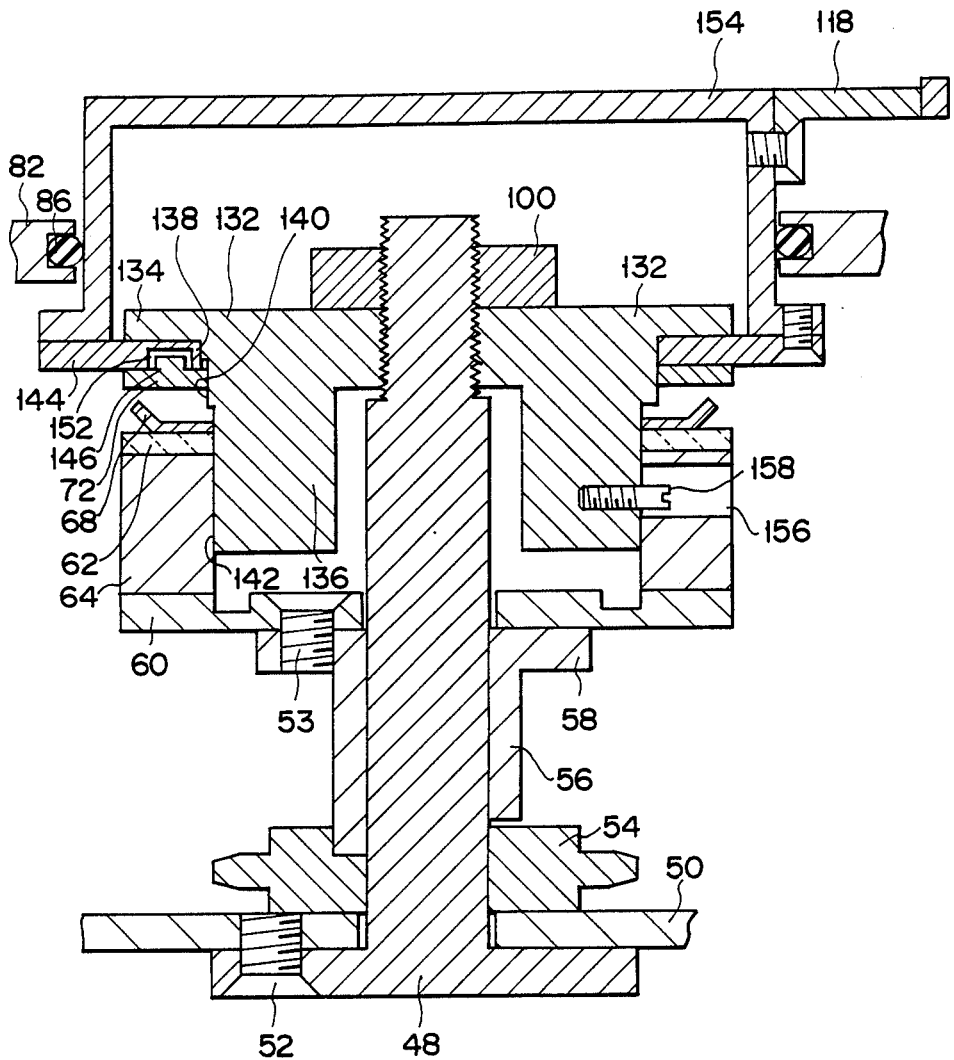

In starting the operation of the endoscope, the insertion section can be bent in the same manner as in the first embodiment if the state shown in FIG. 4 is established. In freeing the insertion section, control lever 118 is rotated to cause grooves 152 and projections 146 engage one another, as shown in FIG. 17. By doing this, the resilience of leaf spring 68 is reduced, so that rotor 60 is disengaged from stator 66. Thus, the insertion section is freed in the same manner as in the first embodiment. According to this second modification, the insertion section can be freed by rotating lever 118 in either direction.

FIGS. 18 to 22 show a second embodiment of the present invention. Endoscope 2 shown in FIG. 21 comprises elongated insertion section 6, and control section 4 is coupled to the proximal end portion of section 6. Flexible universal cord 8 extends from control section 4, and connector 9 is attached to the distal end of cord 8. In insertion section 6, distal end portion 14, bending portion 12, and flexible tube portion 10 are connected in succession. Eyepiece section 15 is attached to the rear end portion of control section 4. Section 4 carries, on its flank, upward bending control switch 166, downward bending control switch 168, leftward bending control switch 170, and rightward bending control switch 172, as well as air-water feed switch 162 and suction switch 164.

Bending portion 12 of insertion section 6 is constructed as shown in FIG. 22. It includes a number of joint links 20 which, each formed of a short tubular structure, are coupled to one another so as to be rockable in both vertical and horizontal directions. A pair of coupling pieces 20A are formed at one end of each joint link 20, while a pair of coupling pieces 20B are formed at the other end of link 20 so that they are circumferentially deviated by 90° from pieces 20A. The respective pairs of coupling pieces 20A and 20B of each two adjacent joint links 20 are linked by means of support shafts 21, individually. The coupling pieces protrude only from the one end face of each of leading and trailing joint links 20F and 20R. Thus, bending portion 12, composed of the joint links coupled in this manner, can be bent in both vertical and horizontal directions.

Cylindrical wire fixing portions 34 are formed on the inner peripheral surface of leading joint link 20F, at four positions at circumferential distances of 90° C from one another, corresponding to the bending directions of bending portion 12. One end of one of four bending wires 32 is inserted in through hole 34A of each wire fixing portion 34, and is fixed firmly by soldering or the like. The other end portions of wires 32 are connected individually to four wire drive units 174 (174A, 174B, 174C and 174D) which are attached to the inner surface of trailing joint link 20R or flexible tube 10, at positions spaced at regular angles of 90° C. Each drive unit 174 includes a linear vibration-wave motor as bending drive means.

Figure 18:
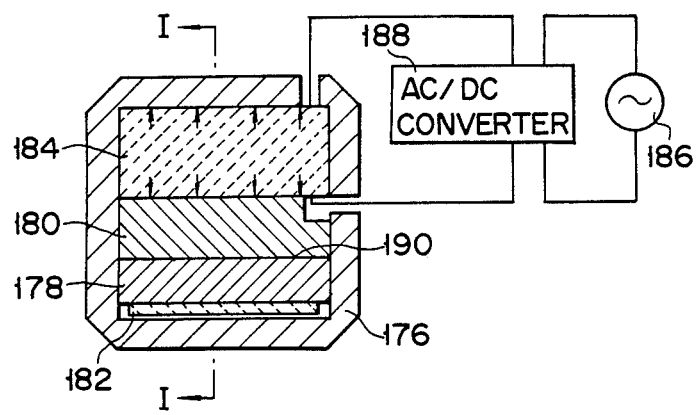
FIGS. 18 and 20 are cross-sectional views of a wire drive unit of an endoscope according to a second embodiment of the present invention.
Figure 19:
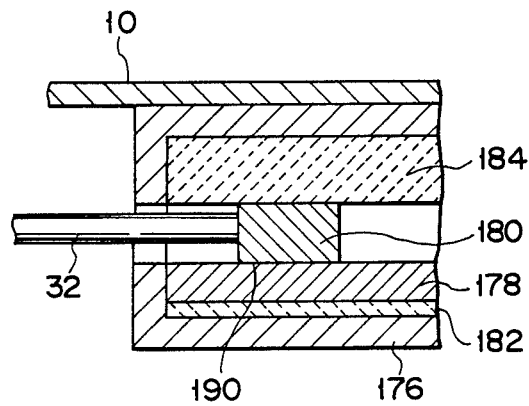
FIG. 19 is a sectional view taken along line I—I of FIG. 18.

Bending portion 12 of insertion section 6 can be bent by means of bending wires 32 and wire drive units 174 each including the linear vibration-wave motor. Unit 174 is shown in FIGS. 18 and 19.

Each wire drive unit 174 is composed of a linear vibration-wave motor, which comprises sheathing 176 formed of a square pipe member, vibrator 178 as a stator housed in sheathing 176, piezoelectric body 182 for generating progressive waves on vibrator 178, and moving body 180 as a rotor in contact with vibrator 178 and coupled with one end of each bending wire 32. Piezoelectric body 182 is driven by means of an AC power source. Housed in sheathing 176, moreover, is laminate-type piezoelectric body 184 in contact with the outer surface of moving body 180. Sheathing 176 may alternatively be cylindrical in shape. Vibrator 178 and piezoelectric bodies 182 and 184 have a length substantially equal to the axial length of sheathing 176, while moving body 180 is long enough to cause bending portion 12 to bend.

Figure 20:
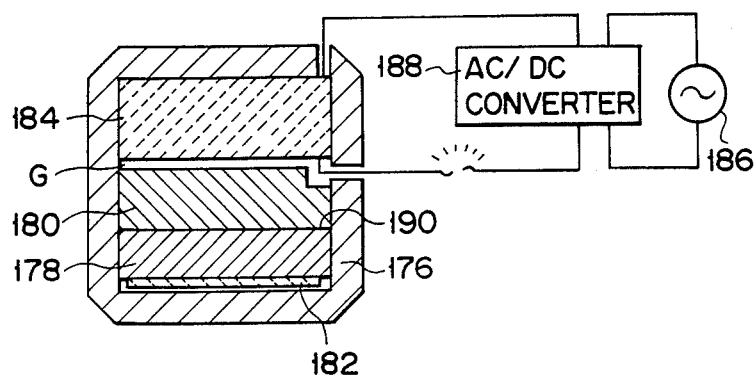
Figure 21:
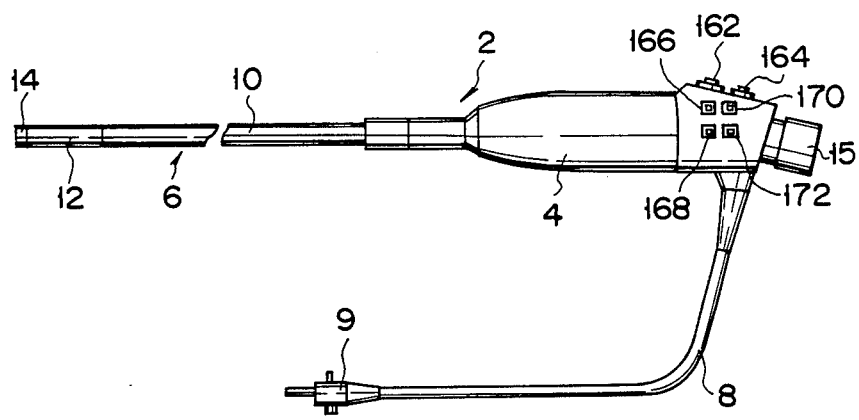
FIG. 21 is a side view of the endoscope according to the second embodiment.

Laminate-type piezoelectric body 184 is fixed to the inner wall surface of sheathing 176 by e.g. adhesive bonding. It is supplied with a DC voltage which is obtained by converting an AC voltage from AC power source 186, for use as an ordinary power source, by means of AC/DC converter 188. If it is not supplied with the DC voltage, piezoelectric body 184 is contracted and displaced so that gap G is produced, as shown in FIG. 20. Accordingly, moving body 180 is allowed to be freely moved by an external force applied thereto by means of wire 32. Wire drive unit 174 further includes means for releasing vibrator 178 and moving body 180 of the vibration-wave motor from the pressure contact.

The following is a description of the operation of the endoscope according to the second embodiment. In starting the operation of endoscope 2, connector 9 of universal cord 8 is first connected to a light source unit (not shown) and AC power source 186. Thereupon, an AC voltage from power source 186 is converted into a DC voltage by means of AC/DC converter 188, and is then applied to laminate-type piezoelectric bodies 184 of wire drive units 174A to 174D. Supplied with the DC voltage in this manner, each piezoelectric body 184 is displaced so as to press moving body 180 against vibrator 178. As a result, a strong frictional force is produced between moving body 180 and vibrator 178, and drive units 174A to 174D are ready to operate as a vibration-wave motor.

If bending portion 12 is expected to be bent upward, for example, bending control switch 166 is operated. Thereupon, piezoelectric bodies 182 of wire drive units 174A and 174C produce progressive waves on ultrasonic vibration surfaces 190 of their corresponding vibrators 178. The progressive waves from units 174A and 174C advance in opposite directions. Thus, moving bodies 180 are driven, and bending wires 32, which are connected at one end to their corresponding moving bodies, are moved, so that bending portion 12 is bent upward.

If the supply circuit is disconnected, as shown in FIG. 20, or in case of power failure, the DC voltage ceases from being applied to laminate-type piezoelectric body 184. Accordingly, body 184 contracts, thereby producing gap G, so that the friction between moving body 180 and vibrator 178 is reduced. As a result, moving body 180 is allowed to be freely moved by an external force applied by means of bending wire 32. Thus, bending portion 12 is freed, so that insertion section 6 can be safely removed from a patient's body.

Figure 24:
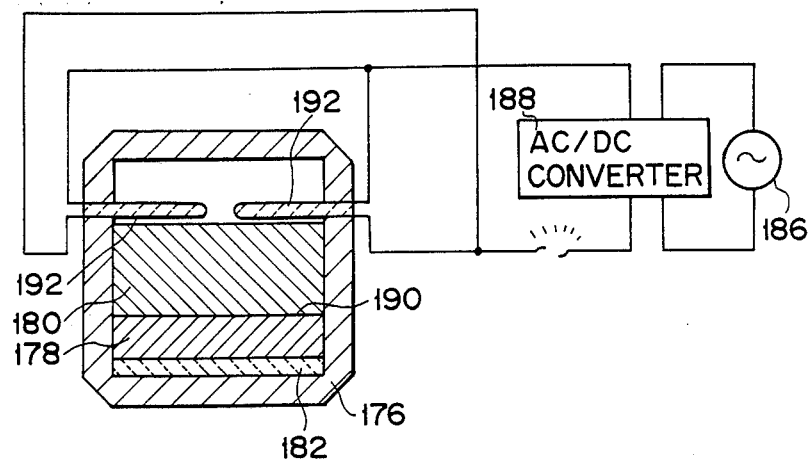

FIGS. 23 and 24 show a first modification of the second embodiment. In this modification, laminate-type piezoelectric body 184 according to the second embodiment is replaced with a pair of planar bimorph-type piezoelectric bodies 192.

Bimorph-type piezoelectric bodies 192 are fixed in the form of a cantilever to the opposite side walls of sheathing 176, individually. The width of each piezoelectric body 192 is substantially equal to the axial length of sheathing 176.

When the endoscope is in the normal operation, as shown in FIG. 23, an AC voltage from AC power source 186 is converted into a DC voltage by means of AC/DC converter 188, and is then applied to both bimorph-type piezoelectric bodies 192. As a result, piezoelectric bodies 192 are displaced so as to press moving body 180 against vibrator 178. Thus, moving body 180 and vibrator 178, in pressure contact with each other, are ready to operate as a vibration-wave motor.

If the control circuit suffers trouble due to disconnection, as shown in FIG. 24, or in case of power failure, bimorph-type piezoelectric body 192 ceases from being supplied with the DC voltage, so that its displacement is zero. Accordingly, moving body 180 is allowed to be freely moved by an external force.

Figure 25:
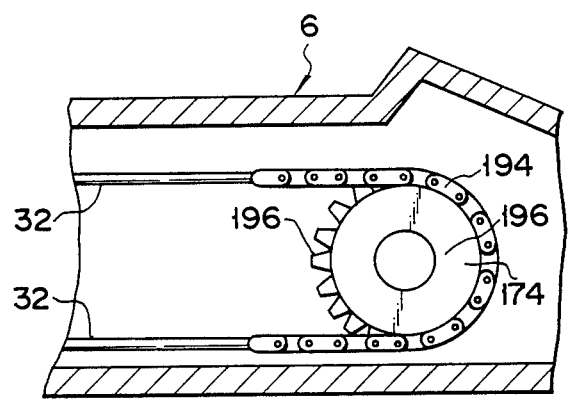
FIG. 25 is a side view of the interior of a control section according to a second modification of the second embodiment.
Figure 26:
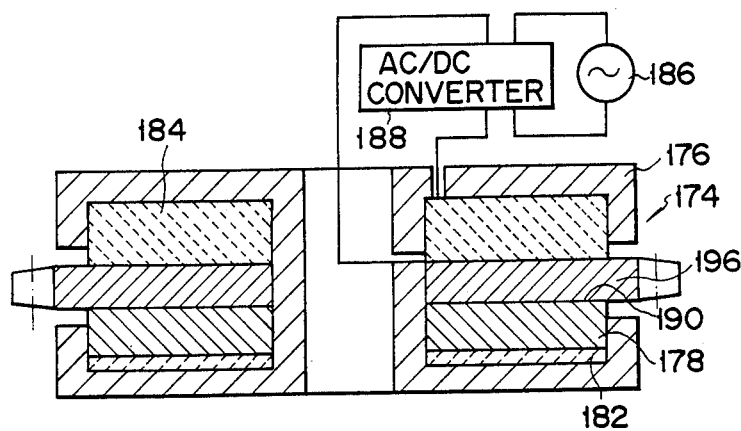
FIG. 26 is a sectional view of a wire drive unit according to the second modification of the second embodiment.

FIGS. 25 and 26 show a second modification of the second embodiment. In this modification, a vertical pair of bending wires 32 extend into control section 4, and are coupled individually to two opposite ends of chain 194. Chain 194 is in engagement with sprocket 196 of circular wire drive unit 174 in section 4. Likewise, a horizontal pair of bending wires 32 are coupled to another chain (not shown), which is in engagement with a sprocket of another circular wire drive unit in control section 4.

As shown in FIG. 26, wire drive unit 174 is composed of a disk-shaped vibration-wave motor, which comprises sheathing 176 formed of a cylindrical member, vibrator 178 housed in sheathing 176, piezoelectric body 182 for generating progressive waves on vibrator 178, sprocket 196 as a rotor in contact with vibrator 178, and laminate-type piezoelectric body 184 in contact with sprocket 196. Piezoelectric body 184 may be one which includes strip-shaped elements arranged radially.

Laminate-type piezoelectric body 184 is fixed to sheathing 176 by e.g. adhesive bonding. It is supplied with a DC voltage which is obtained by converting an AC voltage from AC power source 186, for use as an ordinary power source, by means of AC/DC converter 188. If piezoelectric body 184 is not supplied with the DC voltage, sprocket 196 is allowed to be freely moved by a external force applied thereto by means of bending wire 32 and chain 194.

If piezoelectric body 184 is supplied with the DC voltage, it is displaced so as to press sprocket 196 against vibrator 178. Thus, sprocket 196 is ready to operate as a vibration-wave motor.

If bending portion 12 is expected to be bent upward, for example, bending control switch 166 is operated. Thereupon, piezoelectric body 182 produces progressive waves on ultrasonic vibration surface 190 of vibrator 178. As a result, sprocket 196 rotates, and bending wire 32 are moved, so that bending portion 12 is bent.

If the power supply from the power source is stopped on account of power failure or the like, laminate-type piezoelectric body 184 ceases from being supplied with the DC voltage, so that its displacement is zero. Accordingly, there is no force to press sprocket 196 against vibrator 178, so that sprocket 196 is allowed to be freely moved by an external force. Thus, insertion section 6 can be safely removed from the patient's body.

In this modification, wire drive unit 174 is disposed inside control section 4, so that insertion section 6 can be reduced in diameter.

Figure 27:
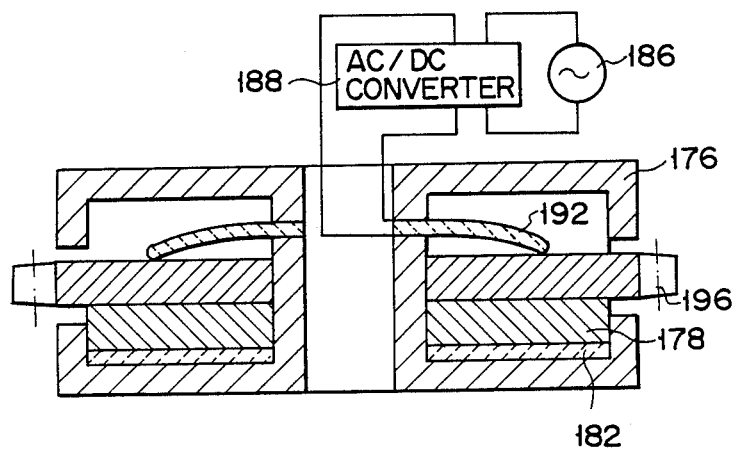
FIG. 27 is a sectional view of a wire drive unit according to a third modification of the second embodiment.

FIG. 27 shows a third modification of the second embodiment. In this modification, laminate-type piezoelectric body 184 according to the second modification is replaced with a pair of bimorph-type piezoelectric bodies 192. Piezoelectric bodies 192 are fixed in the form of a cantilever to the inner walls of sheathing 176, individually. Alternatively, the piezoelectric body may be one which includes strip-shaped elements arranged radially.

Figure 28:
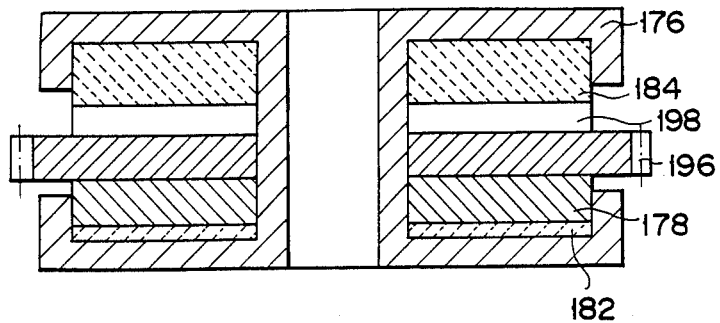
FIG. 28 is a sectional view of a wire drive unit according to a fourth modification of the second embodiment.

FIG. 28 shows a fourth modification of the second embodiment. In this modification, low-friction member 198 is disposed between laminate-type piezoelectric body 184 and sprocket 196 of second modification. A similar low-friction member may be also attached to that surface of piezoelectric body 184 of the second embodiment on the moving body side or the distal end of bimorph-type piezoelectric body 192 according to the first or third modification.

With use of low-friction member 198, the frictional force between laminate-type piezoelectric body 184 and sprocket 196 can be kept low enough to prevent a loss of the rotatory force of the sprocket, even when the piezoelectric body urge the sprocket.

Figure 29:
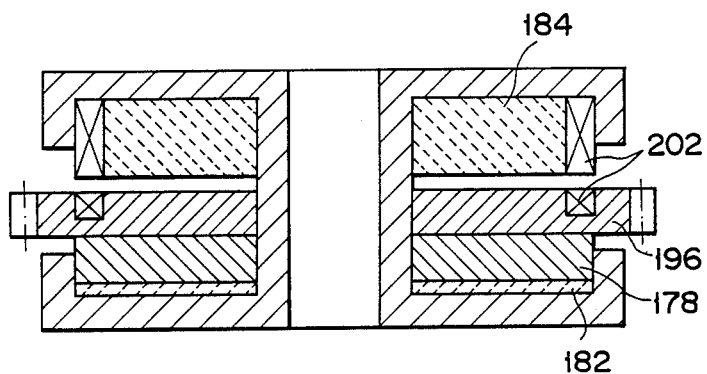
FIG. 29 is a sectional view of a wire drive unit according to a fifth modification of the second embodiment.

FIG. 29 shows a fifth modification of the second embodiment. In this modification, laminate-type piezoelectric body 184 of the second modification is replaced with electromagnet 200, which is provided with coil 202. Sprocket 196 is also provided with coil 202, thus forming an electromagnet. The pole phase of the sprocket side of electromagnet 200 is identical with that of the electromagnet side of sprocket 196. Moreover, laminate-type piezoelectric body 184 and moving body 180 of the first embodiment may be replaced with an electromagnet each.

In this modification, sprocket 196 and electromagnet 200 normally face each other with the same pole phase, so that they repel each other. Thus, sprocket 196 is urged toward vibrator 178 to be ready to operate as a vibration-wave motor.

If the power supply is stopped on account of power failure or the like, no repulsive force is produced between electromagnet 200 and sprocket 196, so that the sprocket is allowed to be freely moved by an external force.

Figure 30:
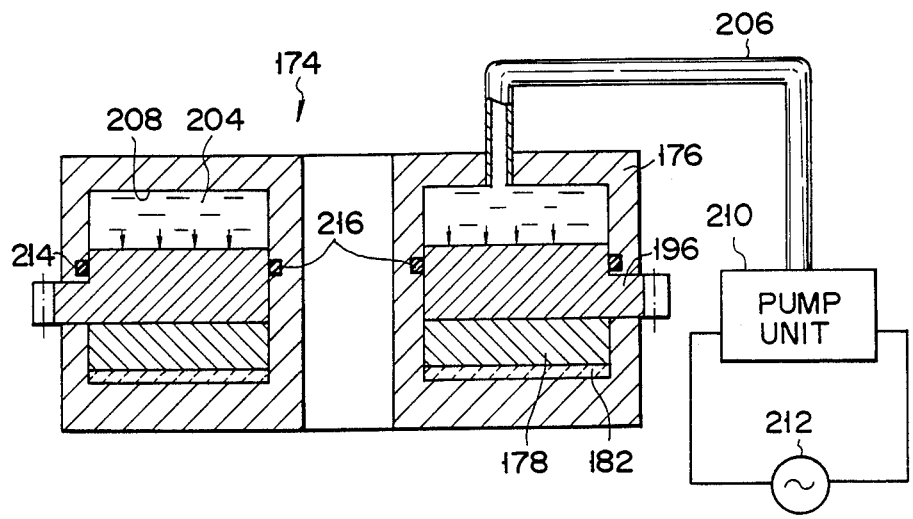
FIG. 30 is a sectional view of a wire drive unit according to a sixth modification of the second embodiment.

FIG. 30 shows a sixth modification of the second embodiment. In this modification, laminate-type piezoelectric body 184 of the second modification is replaced with fluid 204, fluid pump unit 210 for feeding fluid 204 through pipe 206 into space 208 inside sheathing 176, and power source 212 for driving pump unit 210.

O-rings 214 and 216 are interposed between sheathing 176 and sprocket 196, whereby fluid 204 is prevented from leaking from space 208 inside the sheathing.

Normally, in this modification, fluid pump unit 210 is driven by means of power source 212 to feed fluid 204 through pipe 206 into space 208 of wire drive unit 174. Sprocket 196 is pressed against vibrator 178 by means of the pressure of the fluid in space 208 inside sheathing 176. Thus, sprocket 196 is ready to operate as a vibration-wave motor.

If the power supply is interrupted due to power failure or the like, during an endoscopic examination, fluid pump unit 210 is stopped, so that the fluid pressure inside space 208 lowers. Thus, sprocket 196 is allowed to be freely moved by an external force.

In this modification, the rotor is pressed against the stator by means of fluid 204, so that the rotatory force of the rotor is subject to a smaller loss.

Figure 31:
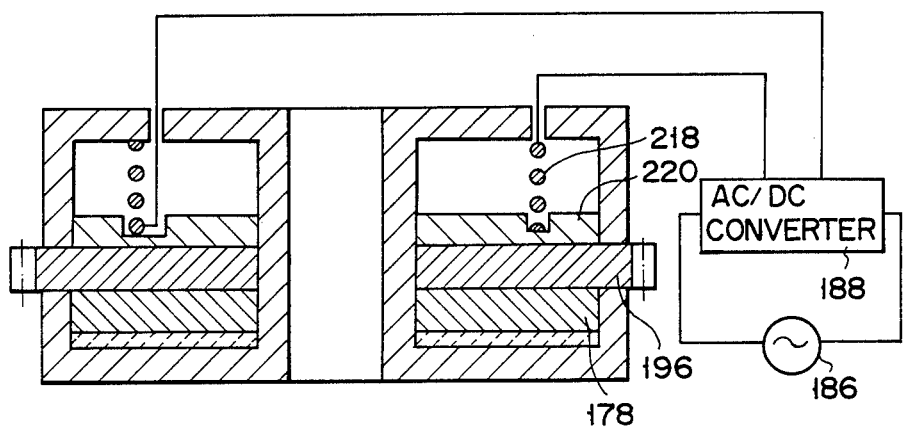

FIGS. 31 and 32 show a seventh modification of the second embodiment. In this modification, laminate-type piezoelectric body 184 of the second embodiment is replaced with spring 218 made of a shape member alloy (SMA) and urging plate 220 fixed to one end of the SMA spring. Spring 218 may be replaced with laminate-type piezoelectric body 184 of the first embodiment.

Normally, in this modification, SMA spring 218 is supplied with a DC voltage from a combination of AC power source 186 and AC/DC converter 188. Spring 218 generates heat by its own resistance, and is deformed so as to press sprocket 196 against vibrator 178 through the medium of urging plate 220. Thus, sprocket 196 and vibrator 178 are ready to operate as a vibration-wave motor.

If the power supply to SMA coil 218 is stopped due to disconnection or the like, as shown in FIG. 32, the temperature of the spring lowers, whereupon the spring is restored to its original shape. Thus, sprocket 196 is allowed to be freely moved by an external force.

Referring now to FIGS. 33 to 37, a third embodiment of the present invention will be described.

In the description of the third embodiment to follow, like reference numerals are used to designate the same members as those of the endoscope according to the second embodiment.

Figure 33:
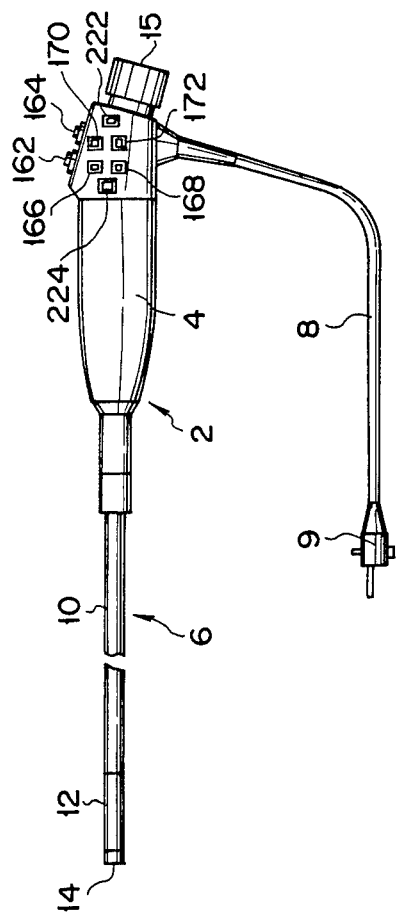
FIG. 33 is a side view of an endoscope according to a third embodiment of the present invention.
Figure 34:
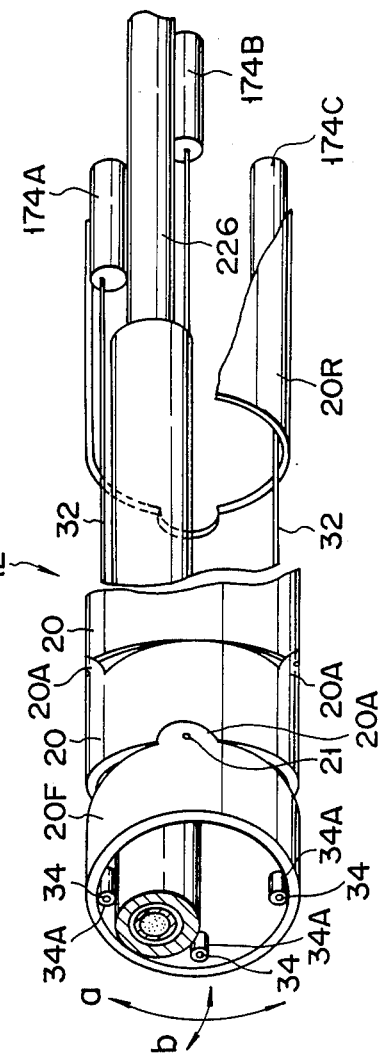
FIG. 34 is a partial sectional view of an insertion section shown in FIG. 33.

As shown in FIG. 33, control section 4 of an endoscope of this embodiment is additionally provided with changeover switch 222 for shifting between an angle-lock mode and an angle-free mode, and emergency power switch 224. Further, insertion section 6 is provided with wire drive units 174, composed of linear vibration-wave motors, and image guide 226. Drive units 174 may alternatively be composed of ring-type vibration-wave motors.

Figure 35:
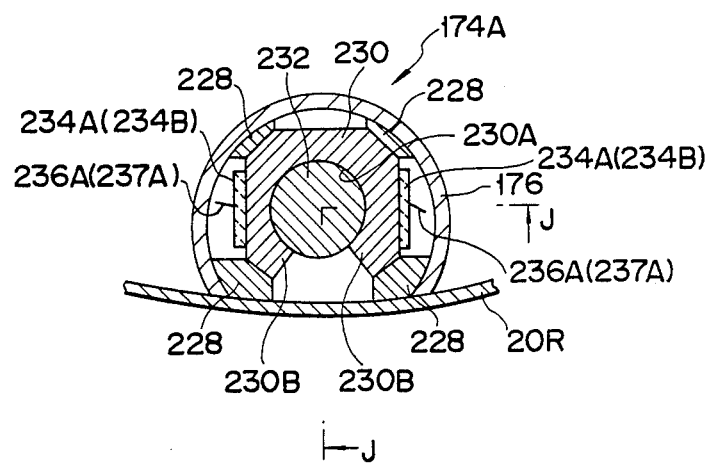
FIG. 35 is a cross-sectional view of a wire drive unit shown in FIG. 34.

In the endoscope according to the third embodiment, as shown in FIG. 35, sheathing 176 of wire drive unit 174A is formed of a cylindrical pipe member. Four fixing members 228 are arranged at substantially regular circumferential intervals of 90° on the inner peripheral surface of sheathing 176, so as to extend over the whole axial length of the sheathing. Fixing members 228 fixedly support fitting member 230, formed of an elastic vibrator, from four corners. Fitting member 230, which has a length substantially equal to the axial length of sheating 176, is substantially U-shaped in vertical section. More specifically, fitting groove 230A is formed in member 230, extending in the axial direction thereof. Two arms 230B of fitting member 230 are bent inward or toward each other, thus both-sidedly holding coupling rod 232 which is connected to bending wire 32 by e.g. soldering. Rod 232 is intimately in contact with the inner peripheral surface of fitting groove 230A.

Figure 36:
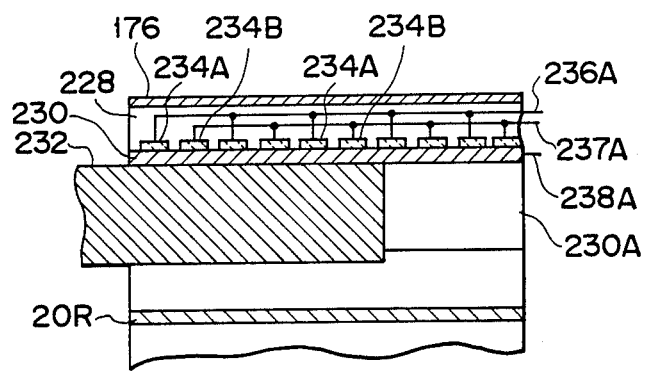
FIG. 36 is a sectional view taken along line J—J of FIG. 35.

As shown in FIG. 36, a number of electrostriction elements 234A and 234B are bonded to each side face of fitting member 230. Elements 234A and 234B are arranged alternately in the axial direction of member 230, at intervals best suited for the generation of standing waves. Elements 234A and 234B are connected to electric wires 236A and 236B, respectively. Also, electric wire 238A is connected to fitting member 230. Other wire drive units 174B, 174C and 174D have the same construction as drive unit 174A.

Figure 37:
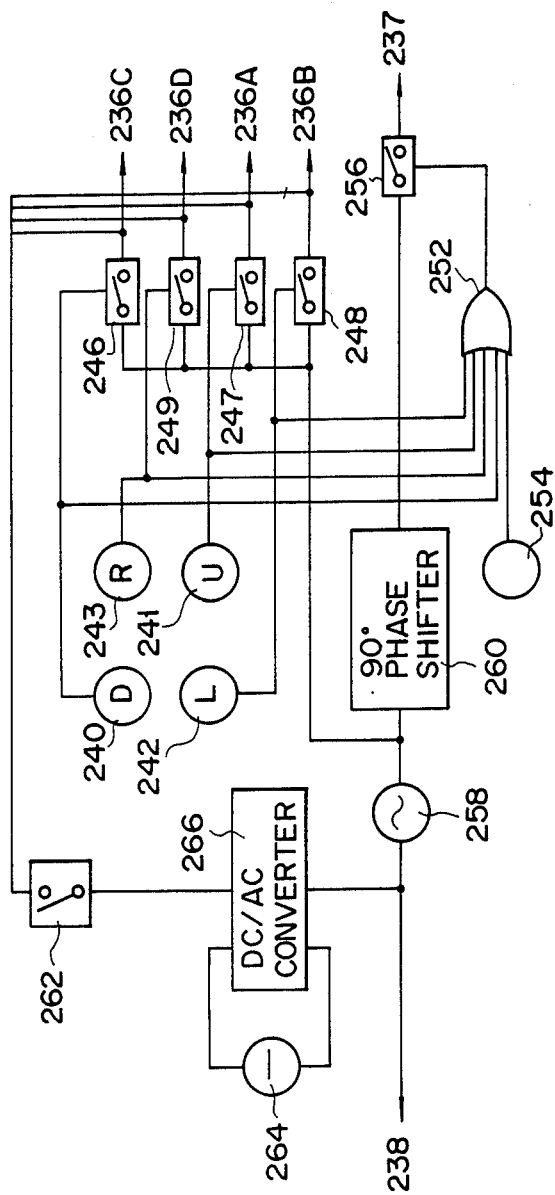
FIG. 37 is a block diagram showing a control circuit of the endoscope according to the third embodiment.

Referring now to FIG. 37, a control circuit, as control means for controlling wire drive units 174, will be described. Switch control circuits 240, 241, 242 and 243, which are provided corresponding to bending control switches 166, 168, 170 and 172, respectively, deliver high- and low-level voltages in response to on-off operations of their corresponding switches. The output terminals of circuits 240, 241, 242 and 243 are connected to control input terminals of switch boxes 246, 247, 248 and 249, respectively, and also to input terminals of OR circuit 252.

Further, switch control circuit 254, which is provided corresponding to changeover switch 222, delivers a high-level voltage in response to angle-free operation, and a low-level voltage in response to angle-lock operation. The output terminal of circuit 254 is connected to an input terminal of OR circuit. The output terminal of circuit 252 is connected to a control input terminal of switch box 256.

Normal-drive power source 258 supplies AC voltage $V = V_0 \cdot \sin(\omega t)$. One end of power source 258 is connected to electric wires 238A to 238D, while the other end thereof is connected to the input terminal of 90°-phase shifter 260 and the respective input terminals of switch boxes 246 to 249. Emergency power source 264, which i connected in parallel with normal-drive power source 258, supplies a DC voltage. One end of power source 264 is connected to electric wires 236A to 236D through DC/AC circuit 266 for converting DC voltage into AC voltage and emergency power switch 262. Electric wires 237A to 237D may be connected in place of wires 236A to 236D. The other end of emergency power source 264 is connected to electric wires 238A to 238D. The respective output terminals of switch boxes 246, 249, 247 and 248 are connected to electric wires 236C, 236D, 236A and 236B, respectively.

Meanwhile, 90°-phase shifter 260 serves to advance the phase of input voltage by 90°. The output terminal of shifter 260 is connected to the input terminal of switch box 256. In switch boxes 246 to 249 and 256, the input and output terminals can be connected and disconnected when the voltage at their control input terminals is at high and low levels, respectively.

The following is a description of the operation of the endoscope according to the third embodiment. First, let us suppose a case such that bending portion 12 is bent upward, and changeover switch 222 is shifted for angle-lock operation. If upward bending control switch 166 is turned on, switch control circuit 241 delivers a high-level voltage, so that switch boxes 247 and 256 conduct. As a result, voltage $V = V_0 \cdot \sin(\omega t)$ is supplied to electric wire 236A, while voltage $V = V_O \cdot \sin(\omega t + \pi/2)$ is supplied to each of electric wires 237A to 237D. At this time, no voltage is supplied to electric wires 236B to 236D, so that standing vibration waves are produced in elastic vibrators or fitting members 230 of wire drive units 174B to 174D. Thus, fitting members 230 are allowed to be easily moved by an external force. Produced in fitting member 230 of wire drive unit 174A, on the other hand, is a vibration wave of the direction in which wire 32 connected to coupling rod 232 is pulled. Thus, wire 32 for upward bending is pulled, so that bending portion 12 is bent upward. If bending control switch 166 is turned off, the voltage ceases to be supplied to fitting members 230 of wire drive units 174, so that bending portion 12 is stopped as it is, and cannot be easily moved by an external force. If bending control switches 168, 170 and 172 are turned on, bending portion 12 can be bent downward, leftward, and rightward, respectively.

If changeover switch 222 is shifted for angle-free operation, switch control circuit 254 delivers a high-level voltage, so that the input and output terminals of switch box 256 are in the normal state. Accordingly, voltage $V = V_0 \cdot \sin(\omega t + \pi/2)$ is continually applied to fitting members 230 of wire drive units 174, so that standing vibration waves are continually produced. If bending control switch 166 is turned on in this state, for example, bending portion 12 is bent upward in the same manner as in the case of the aforementioned angle-lock operation.

If the voltage supply from normal-drive power source 258 is stopped on account of power failure or the like, electric wires 236A to 236D can start to be supplied with voltage by manually turning on emergency power switch 258. Thereupon, standing waves are produced in elastic vibrators or fitting members 230 of wire drive units 174A to 174D, so that members 230 are allowed to be easily moved by an external force. Thus, insertion section 6 can be safely removed from the body cavity.

FIG. 38 shows a first modification of the third embodiment. In this modification, battery 268 is used as the DC power source for the third embodiment. As regards the arrangement of other elements, there is no difference between this modification and the third embodiment.

FIG. 39 shows a second modification of the third embodiment. In this modification, the DC power source for the third embodiment includes generator 270 driven by means of normal-drive power source 258, and battery 272 which charges itself with electricity supplied from generator 270. Unlike battery 268, and 272 need not be replaced on account of its chargeability.

Figure 40:
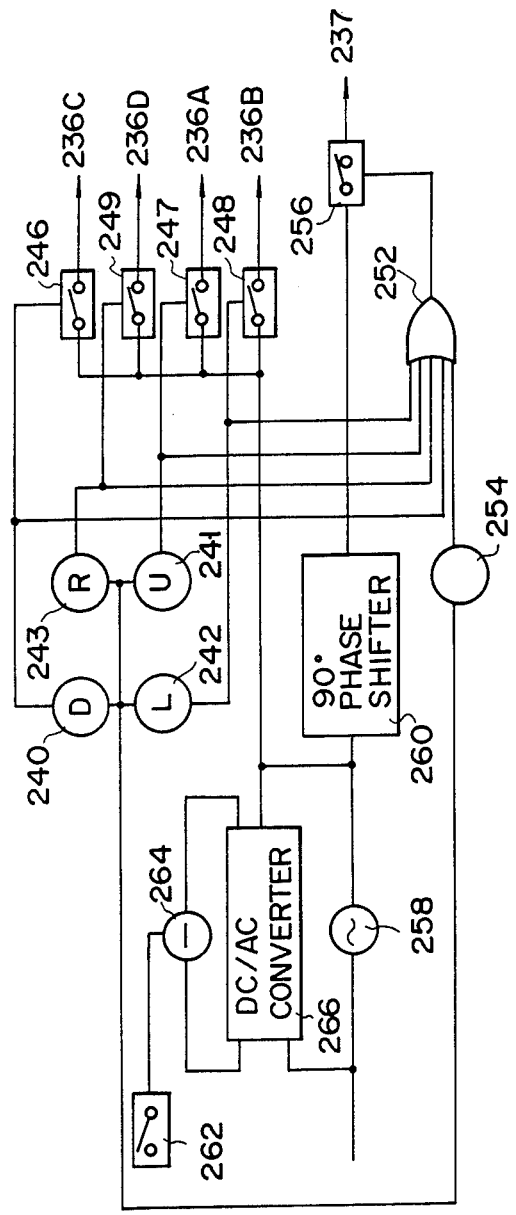
FIG. 40 is a block diagram of a control circuit according to a third modification of the third embodiment.

FIG. 40 shows a third modification of the third embodiment. In this modification, emergency power source 264, which is connected in parallel with normal-drive power source 258, is connected to DC/AC circuit 266 for converting a DC voltage supplied thereto into an AC voltage, switch boxes 246 to 249, and 90°-phase shifter 260. Power source 246 supplies a DC voltage to switch control circuits 240 to 243 and 254 through emergency power switch 262.

In this modification, if the voltage supply from normal-drive power source 258 is stopped on account of power failure, for example, emergency power switch 262 is manually turned on. By doing this, a DC voltage is supplied to switch control circuits 240 to 243 and 254; AC voltages $V = V_0 \cdot \sin(\omega t)$ to switch boxes 246 to 248, and $V = V_0 \cdot \sin(107\ t + \pi/2)$ to switch box 256. Thus, bending portion 12 is driven by optionally operating control circuits 240 to 243 and 254. In case of power failure or the like, according to this modification, angle operation can be performed as well as angle-free operation.

Figure 41:
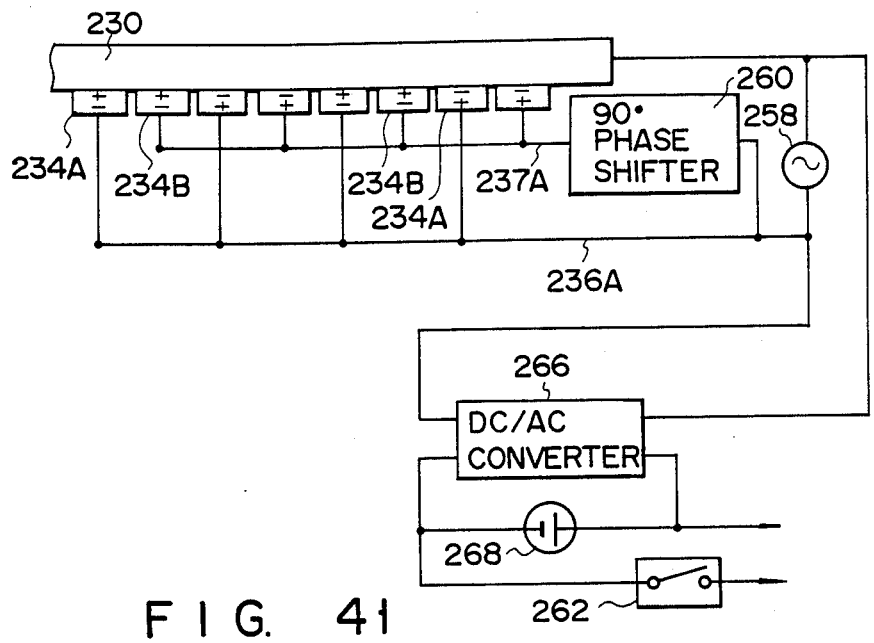
FIG. 41 is a block diagram of a control circuit according to a fourth modification of the third embodiment.

FIG. 41 shows a fourth modification of the third embodiment. In this modification, battery 268 is used as the DC power source for the third modification.

Figure 42:
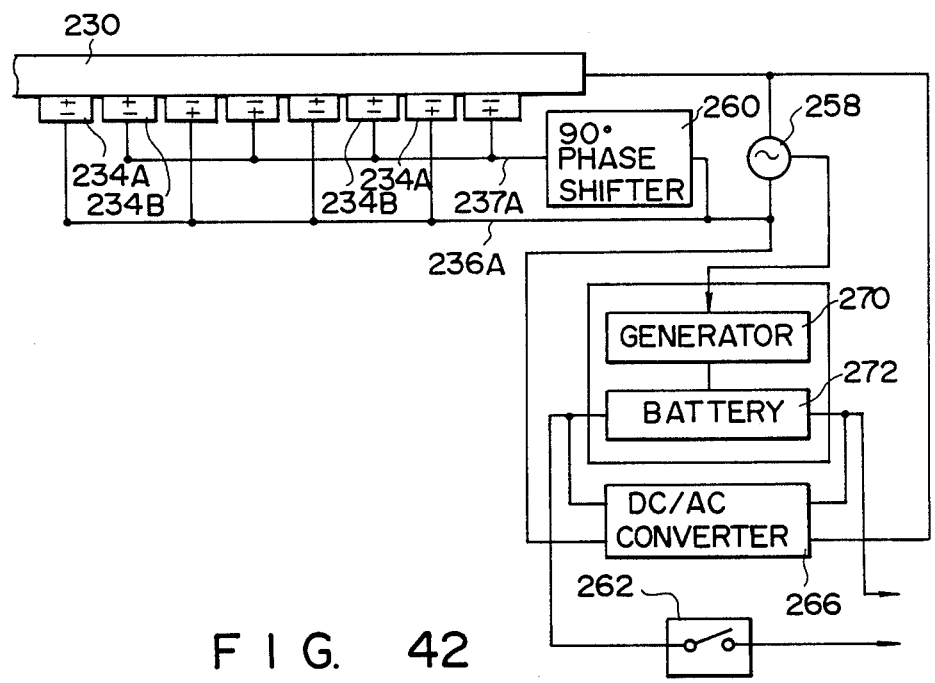
FIG. 42 is a block diagram of a control circuit according to a fifth modification of the third embodiment.

FIG. 42 shows a fifth modification of the third embodiment. In this modification, the DC power source for the third modification includes generator 270 driven by means of normal-drive power source 258, and battery 272 which charges itself with electricity supplied from generator 270. Also in this case, angle operation can be performed as well as angle-free operation. Unlike the battery, moreover, battery 272 need not be replaced.

Figure 43:
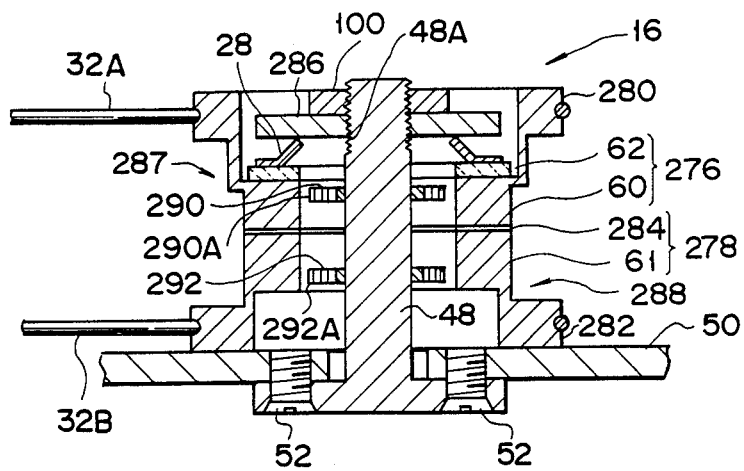
FIG. 43 is a longitudinal sectional view of a bending control unit of an endoscope according to a fourth embodiment of the present invention.
Figure 44:
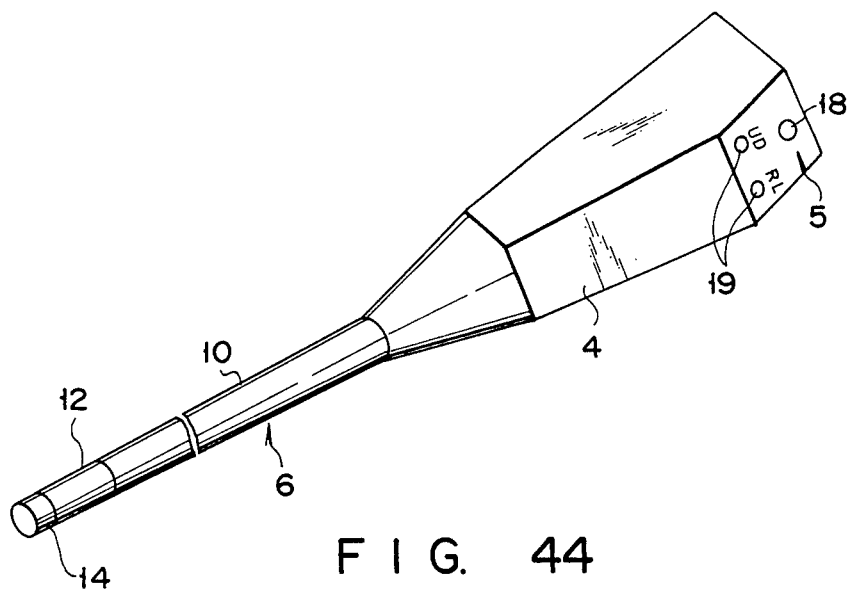
FIG. 44 is a perspective view of the endoscope according to the fourth embodiment.

FIGS. 43 and 44 shows a fourth embodiment of the present invention. Endoscope 2 shown in FIG. 44 comprises control section 4 and insertion section 6. Insertion section 6 includes flexible portion 10, bending portion 12, and distal end structure 14. Control section 4 is provided with bending control portion 5 for remotely bending the bending portion. Bending unit 16 contained in control section 4 can be operated by means of bending control portion 5.

As shown in FIG. 43, bending unit 16 has stationary shaft 48. The proximal end portion of shaft 48 is fixed to frame 50 of control section 4 by means of fixing screws 52. First and second rotating bodies 276 and 278 are rotatably fitted in layers on shaft 48. First rotating body 276 is composed of first rotor 60, having first pulley 280, and vibrator 62 in contact with rotor 60. Second rotating body 278 is composed of second rotor 61, having second pulley 282, and slide plate 284 interposed between first and second rotors 60 and 61. Operating wire 32A for vertical bending, for use as a tractive member, is passed around first pulley 280, while operating wire 32B for horizontal bending is passed around second pulley 282. These tractive members are housed in insertion section 6, and their end portions are coupled to a bending mechanism (not shown) contained in bending portion 12. Bending portion 12 can be bent vertically and horizontally by pulling the tractive members.

Screw portion 48A is formed at the distal end portion of stationary shaft 48, and pressure member 286 is fixedly screwed on screw portion 48A. Member 286 is fixed by means of lock nut 100. Belleville spring or ring-shaped urging spring 28 as urging means, made of a shape memory alloy, is provided on the top surface of vibrator 62 which faces the underside of pressure member 286. The lower edge of spring 28 is fixed to the top surface of vibrator 62, while its upper edge is pressed against the underside of member 286.

In the normal operating state, urging spring 28 is supplied with a DC voltage from an AC power source and an AC/DC converter, and generates heat by its own resistance. As a result, spring 28 is deformed so as to press vibrator 62 against first rotor 60, and also to press first rotor 60 against second rotor 61 across slide plate 284. Thus, the forces of pressure contact between vibrator 62 and first rotating body 276 and between first and second rotating bodies 276 and 278 can be freely set by screwing pressure member 286 onto screw portion 48A.

If the power supply to urging spring 28 is interrupted due to disconnection or the like, the temperature of the spring lowers, so that the spring is restored to its original shape. As a result, the rotors are allowed to be freely moved by an external force, so that the insertion section of the endoscope can be safely removed from the body cavity.

First rotating body 276, which is composed of vibrator 62 and first rotor 60, and second rotating body 278, which is composed of second rotor 61 and slide plate 284, constitute ultrasonic motors 287 and 288, respectively.

First and second rotating bodies 276 and 278 are ring-shaped. First and second electromagnets 290 and 292, for use as control means, are mounted on stationary shaft 4 which faces the inner peripheral surfaces of rotating bodies 276 and 278. Electromagnets 290 and 292 are ring-shaped, and attraction surfaces 290A and 292A are formed on the outer peripheral surfaces of electromagnets 290 and 292, respectively, so as to be situated close to first and second rotors 60 and 61. Vibrator 62 is connected to the power source through on-off switch 18 at bending control portion 5 of control section 4. First and second electromagnets 290 and 292 are connected to the power source through changeover switches 19 for four-direction bending control at bending control portion 5.

Thus, first and second rotors 60 and 61, which constitute first and second ultrasonic motors 287 and 288, respectively, can be selectively driven to actuate the bending mechanism by operating on-off switch 18 and changeover switches 19 at control section 4 of the endoscope. Progressive waves may be produced on the surface of vibrator 62 by energizing the vibrator. At this time, if first and second electromagnets 290 and 292 are de-energized and excited, respectively, second rotor 61 is braked to be locked by second electromagnet 292. In response to the progressive waves of vibrator 62, therefore, first rotor 60 rotates relatively to second rotor 61, and this rotation is transmitted to first pulley 280. Thereupon, operating wire 32A for vertical bending, which is passed around pulley 280, is pulled, and the bending mechanism contained in bending portion 12 is actuated by the tractive force. Thus, bending portion 12 can be bent vertically. If first and second electromagnets 290 and 292 are excited and de-energized, respectively, with vibrator 62 energized so that the progressive waves are produced on its surface, first rotor 60 is locked by the agency of electromagnet 290. Accordingly, the progressive waves of vibrator 62 are transmitted through first rotor 60 to second rotor 61, so that rotor 61 rotates. The rotation of rotor 61 is transmitted to second pulley 282. Thereupon, operating wire 32B for horizontal bending, which is passed around pulley 282, is pulled, and the bending mechanism contained in bending portion 12 is actuated by the tractive force. Thus, bending portion 12 can be bent horizontally.

Bending portion 12 can be bent in the opposite direction by reversing the direction of the progressive waves by means of on-off switch 18.

Figure 45:
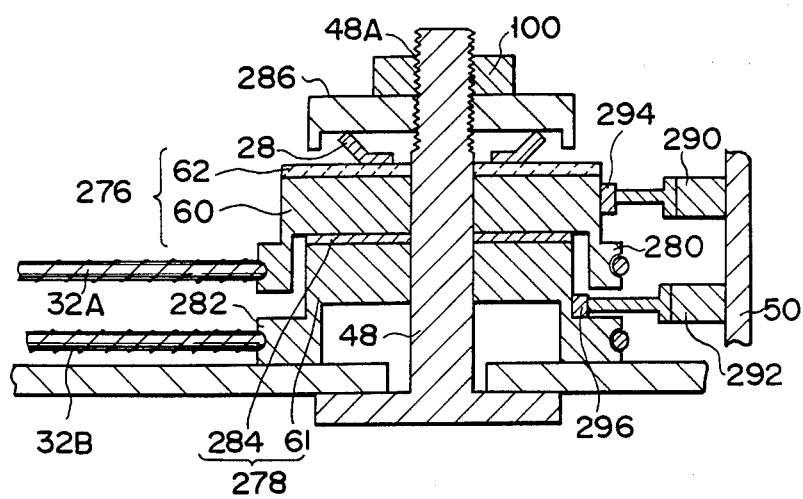
FIG. 45 is a longitudinal sectional view of a bending control unit according to a first modification of the fourth embodiment.

FIG. 45 shows a first modification of the fourth embodiment. In this modification, first and second electromagnets 290 and 292, for use as braking means, are located outside first and second rotors 60 and 61. More specifically, first and second electromagnets 290 and 292 are mounted on frame 50 of control section 4 so as to face the outer peripheral surfaces of first and second rotors 60 and 61, respectively. Electromagnets 290 and 292 are provided with brake shoes 294 and 296, respectively. When these electromagnets are excited, brake shoes 294 and 296 are pressed against the outer peripheral surfaces of first and second rotors 60 and 61, respectively, thereby braking the rotors.

FIGS. 46 to 49 show a second modification of the fourth embodiment. In this modification, first and second rotating bodies 276 and 278 are arranged on a plane perpendicular to the pulling direction of the tractive members.

More specifically, first rotating body 276 includes ring-shaped vibrator 298 and first rotor 300, while second rotating body 278 includes ring-shaped slide plate 302 and second rotor 304. Rotating bodies 276 and 278 are housed in cylindrical casing 306. Formed on one end side of casing 306 is bearing portion 308 which supports second rotor 304 for rotation. Screw portion 312 is formed on the other end side of casing 306, whereby pressure member 310 is fixed by screwing. Urging spring 314, for use as urging means, is disposed in a compressed manner between pressure member 310 and vibrator 298. Two coil pipes 316 are attached to first rotor 300 with a circumferential phase difference of 180° from each other Likewise two coil pipes 318 are attached to second rotor 304 with a circumferential phase difference of 90° from pipes 316. Pipes 316 and 318 extend in the axial direction of first and second rotating bodies 276 and 278, and operating wire 32, for use as a tractive member, is movably passed through each of the coil pipes. Wires 32 can be pulled by rotating first and second rotors 300 and 304.

Figure 46:
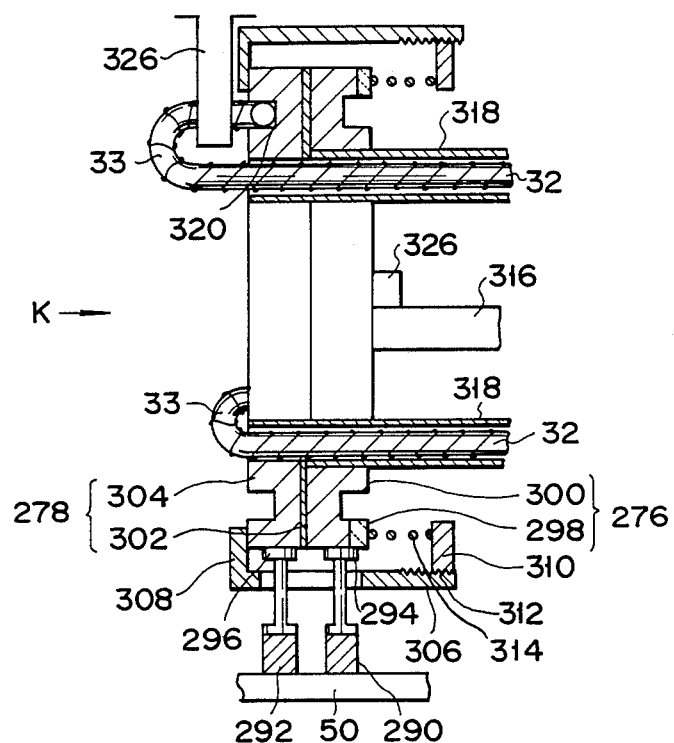
FIG. 46 is a sectional view of a bending control unit according to a second modification of the fourth embodiment.

Since mechanisms for pulling the individual operating wires are constructed in the same manner, only the mechanism for second rotor 304 will be described. As shown in FIG. 46, annular grove 320 is formed in the outer peripheral edge of rotor 304. Groove 320 is wide and deep enough to receive operating wire 32. Further, guide groove 322 is formed at that bottom portion of groove 320 near coil pipe 318. Tip 324, which is fixed to the extreme end portion of wire 32, is movably fitted in groove 322. Stoppers 326 protrude in the radial direction of second rotor 304 from frame 50 of control section 4. Bent portion 33 of wire 32 engages each stopper 326. As first and second rotors 300 and 304, which constitute first and second rotating bodies 276 and 278, respectively, rotate, operating wires 32 coupled to rotors 300 and 304 are pulled.

Figure 47:
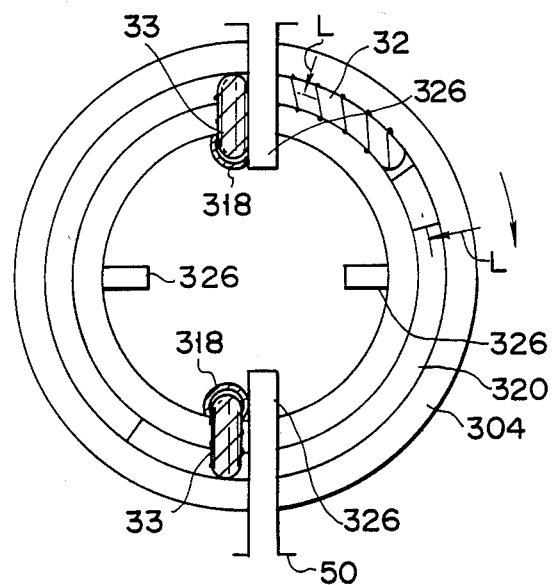
FIG. 47 is a front view taken in the direction of arrow K of FIG. 46.
Figure 48:
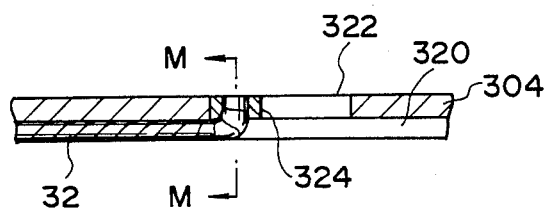
FIG. 48 is a sectional view taken along line L—L of FIG. 47.
Figure 49:
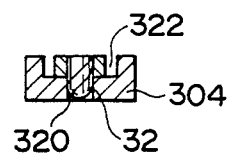
FIG. 49 is a sectional view taken along line M—M of FIG. 48.

More specifically, when second rotor 304 rotates in the direction indicated by the arrow, as shown in FIG. 47, the extreme end portion of operating wire 32 is pulled in the rotating direction through tip 324. Thus, wire 32 is drawn into annular groove 320 with the aid of stopper 326. When rotor 304 rotates in the direction opposite to the direction of the arrow, wire 32 is drawn out of groove 320 while being guided by stopper 326. In this case, the extreme end portion of wire 32 is movably fitted in guide groove 322 with the aid of tip 324. As tip 324 moves in groove 322, therefore, it can absorb slackness of wire 32.

First and second electromagnets 290 and 292, for use as braking means, are located outside first and second rotors 300 and 304. More specifically, first and second electromagnets 290 and 292 are mounted on frame 50 of control section 4 so as to face the outer peripheral surfaces of first and second rotors 300 and 304, respectively. Electromagnets 290 and 292 are provided with brake shoes 294 and 296, respectively. When these electromagnets are excited, brake shoes 294 and 296 are pressed against the outer peripheral surfaces of first and second rotors 300 and 304, respectively, by the repulsive force of the electromagnets, thereby braking the rotors.

The rotating bodies are not limited to two in number, and may be three or more.

Figure 50:
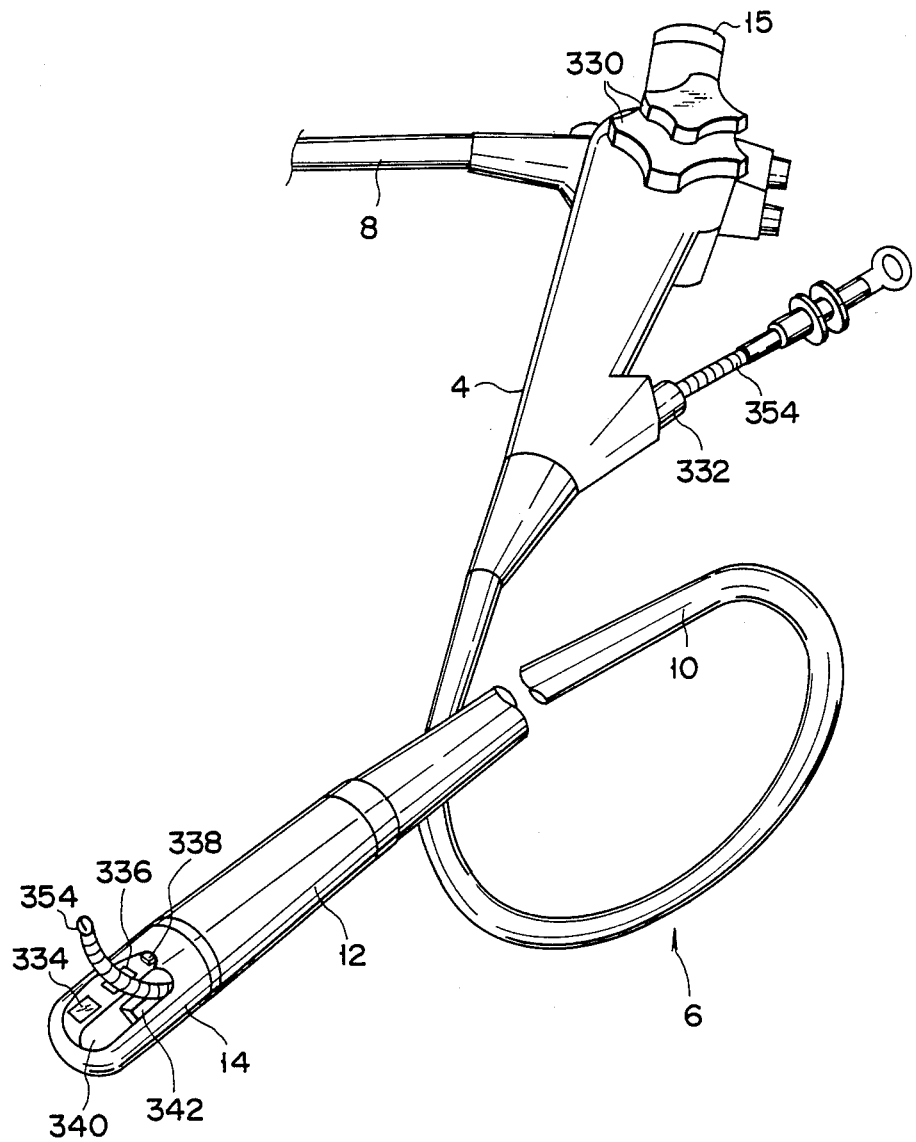
FIG. 50 is a perspective view of an endoscope according to a fifth embodiment of the present invention.
Figure 51:
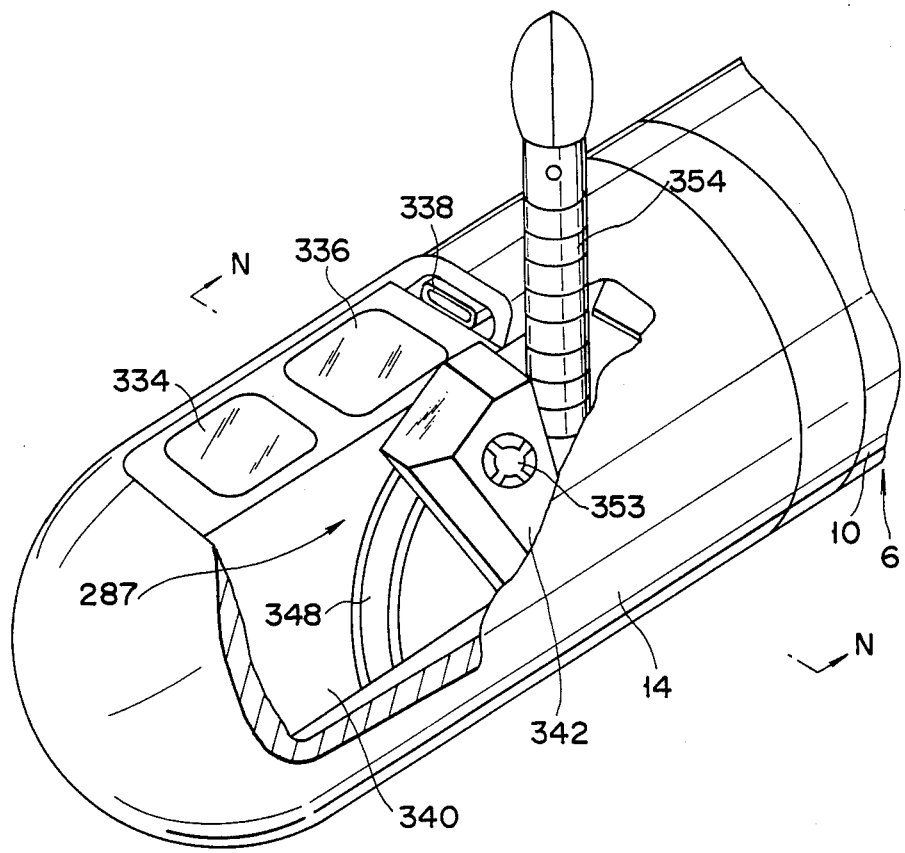
FIG. 51 is a perspective view of a distal end portion of an insertion section shown in FIG. 50.
Figure 52:
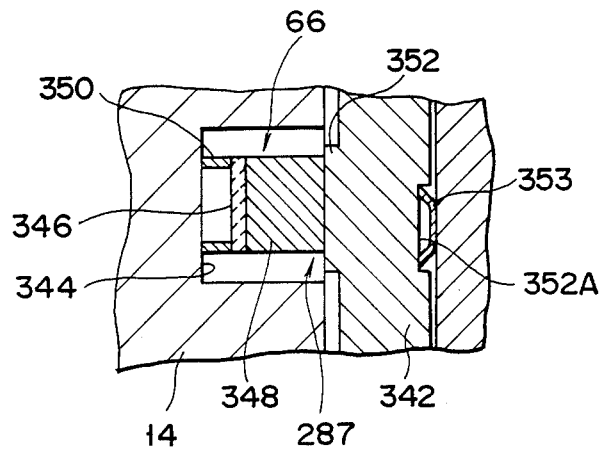
FIG. 52 is a sectional view taken along line N—N of FIG. 51.

FIGS. 50 to 52 show a fifth embodiment of the present invention. An endoscope shown in FIG. 50 comprises control section 4, to which are insertion section 6 and universal cord 8 are coupled. The endoscope further comprises eyepiece section 15, a pair of bending control knobs 330, and instrument port 332.

Distal end structure 14 is attached to flexible tube portion 10 of insertion section 6 by means of bending portion 12. The bending portion can be bent vertically and horizontally by means of knobs 330.

Distal end structure 14 is provided with illumination window 334, view window 336, and nozzle 338, arranged along the axial direction thereof. Nozzle 338 serves to spout cleaning water or air onto the windows. Housing chamber 340 is defined beside the windows and the nozzle. As shown in FIGS. 50 and 51, raising block 324 is housed in chamber 340. One end of block 342 is rockably supported by a support shaft (not shown). Block 342 is rocked by means of ultrasonic motor 287 for use as a drive mechanism. In motor 287, piezoelectric element 346 and elastic body 348, which constitute stator 66, are successively arranged in an arc inside recess 344 which is formed in the inner surface of chamber 340. Stator 66 is backed up by mounting member 350. Elastic body 348 is in contact with ridge 352 formed on one side face of raising block 342. Thus, block 342 serves as a rotor of ultrasonic motor 287. Recess 352A is formed in the other side face of block 342, and spring body 353 made of a shape memory alloy is fitted in recess 352A. Spring body 353 is in contact with the inner surface of chamber 340. In the normal operating state, the spring body is supplied with a DC voltage from an AC power source and an AC/DC converter, and generates heat by its own resistance. As a result, spring body 353 is deformed so as to press the one side face of raising block 342 against the elastic body of stator 66.

If stator 66 is energized, progressive waves are produced along the direction of the circular arc of the stator. Accordingly, raising block 342, for use as the rotor, is rocked along stator 66, and can be kept at a desired rotational angle by the braking function of ultrasonic motor 287. Thus, the projecting direction of instrument 354, which is inserted into chamber 340 through instrument port 332 of control section 4, can be set by means of block 342.

The rocking direction and angle of raising block 342 can be controlled by means of a control device (not shown).

In setting the direction of the projection of instrument 354 from chamber 340, in the endoscope according to this embodiment, raising block 342 can be rocked by energizing stator 66 of ultrasonic motor 287. If the power supply to stator 66 is stopped when a desired angular position is attained by block 342, the block can be held in that position.

If instrument 354 is pushed into the channel therefor after raising block 342 is rocked to a predetermined angular position, it is projected from chamber 340, in a predetermined direction along the top surface of block 342. Thus, the rocking operation for raising block 342 can be achieved easily and quickly by only controlling the power supply to ultrasonic motor 287, without regard to the bending state of insertion section 6.

If the power supply to spring body 353 is interrupted due to disconnection or the like, the temperature of the spring body lowers, so that the spring body is restored to its original shape. As a result, raising block 342 is allowed to be freely moved by an external force, so that instrument 354 can be safely drawn out from the endoscope.

What is claimed is:

1. An endoscope having an insertion section with a moving part, comprising:
   stator means for generating a surface wave as a combination of a transverse wave and a longitudinal wave;
   rotor means rotatably disposed facing said stator means;
   urging means for generating an urging force for bringing said rotor means intimately into contact with said stator means;
   coupling means coupled to said rotor means for causing said moving part of the endoscope to operate as said rotor means rotates; and
   disengaging means for weakening said urging force generated by said urging means, for thereby releasing said stator means and said rotor means from said intimate contact with each other to thereby permit said rotor means to rotate relative to said stator means when said urging force is weakened by said disengaging means.

2. The endoscope according to claim 1, wherein said moving part includes a bending portion attached to a distal end portion of the insertion section.

3. The endoscope according to claim 1, wherein said moving part includes instrument guide means for guiding an instrument, said guide means extending from a distal end portion of the insertion section.

4. The endoscope according to claim 1, wherein said urging means and said disengaging means include a piezoelectric element connected to an electric power source unit.

5. The endoscope according to claim 1, further comprising a main electric power source unit connected to said stator means.

6. The endoscope according to claim 5, wherein said urging means and said disengaging means include means for bringing said rotor means and said stator means intimately into contact with each other when electric power is supplied from said power source unit to said stator means, and for releasing said rotor means and said stator means from said intimate contact with each other when the supply of electric power is interrupted.

7. The endoscope according to claim 5, wherein said urging means and said disengaging means include an emergency DC power source unit connected in parallel with said main power source unit, a DC/AC converter circuit connected to said DC power source unit, and switch means for switching between said main power source unit and said DC power source unit.

8. The endoscope according to claim 1, wherein said rotor means includes first and second rotor elements for operating said moving part in different directions, and said urging means and said disengaging means include rotation stopping means for selectively stopping the rotation of either of said first and second rotor elements.

9. The endoscope according to claim 1, wherein said urging mean and said disengaging means include a spring made of a shape memory alloy and connected to an electric power source unit.

10. The endoscope according to claim 1, wherein said disengaging means includes means operable from outside said endoscope for releasing said stator means and said rotor means from said intimate contact with each other.

11. The endoscope according to claim 10, further comprising a main electric power source unit connected to said stator means.

12. The endoscope according to claim 11, wherein said urging means and said disengaging means include means for bringing said rotor means and said stator means intimately into contact with each other when electric power is supplied from said power source unit to said stator means, and for releasing said rotor means and said stator means from said intimate contact with each other when the supply of electric power is interrupted.

13. The endoscope according to claim 11, wherein said urging means and said disengaging means include an emergency DC power source unit connected in parallel with said main power source unit, a DC/AC converter circuit connected to said DC power source unit, and switch means for switching between said main power source unit and said DC power source unit.

14. The endoscope according to claim 10, wherein said rotor means includes first and second rotor elements for operating said moving part in different directions, and said urging means and said disengaging means include rotation stopping means for selectively stopping the rotation of either of said first and second rotor elements.

15. The endoscope according to claim 1, wherein said disengaging means includes means responsive to an occurrence of a power failure or an electrical malfunction for releasing said stator means and said rotor means from said intimate contact with each other.

16. The endoscope according to claim 15, further comprising a main electric power source unit connected to said stator means.

17. The endoscope according to claim 16, wherein said urging means and said disengaging means include means for bringing said rotor means and said stator means intimately into contact with each other when electric power is supplied from said power source unit to said stator means, and for releasing said rotor means and said stator means from said intimate contact with each other when the supply of electric power is interrupted.

18. The endoscope according to claim 16, wherein said urging means and said disengaging means include an emergency DC power source unit connected in parallel with said main power source unit, a DC/AC converter circuit connected to said DC power source unit, and switch means for switching between said main power source unit and said DC power source unit.

* * * * *

UNITED STATES PATENT AND TRADEMARK OFFICE
CERTIFICATE OF CORRECTION

PATENT NO. : 4,924,852
DATED      : May 15, 1990
INVENTOR(S): SUSUKI et al

It is certified that error appears in the above-identified patent and that said Letters Patent is hereby corrected as shown below:

Title Page, Section [75] Inventors:

Change the addresses of the following two inventors to read as follows:

--Masaaki HAYASHI, Tokyo-- and

--Hideo ADACHI, Iruma--.

Signed and Sealed this

Twenty-second Day of June, 1993

Attest:

MICHAEL K. KIRK

Attesting Officer

Acting Commissioner of Patents and Trademarks